US008106255B2

(12) United States Patent
Carroll et al.

(10) Patent No.: US 8,106,255 B2
(45) Date of Patent: Jan. 31, 2012

(54) TARGETED CHROMOSOMAL MUTAGENASIS USING ZINC FINGER NUCLEASES

(76) Inventors: Dana Carroll, Salt Lake City, UT (US); Maria Bibikova, San Diego, CA (US); Gary N. Drews, Salt Lake City, UT (US); Kent Gregory Golic, Salt Lake City, UT (US); Mary M. Golic, Salt Lake City, UT (US)

(*) Notice: Subject to any disclaimer, the term of this patent is extended or adjusted under 35 U.S.C. 154(b) by 1479 days.

(21) Appl. No.: 10/502,565

(22) PCT Filed: Jan. 22, 2003

(86) PCT No.: PCT/US03/02012
§ 371 (c)(1),
(2), (4) Date: Jul. 22, 2004

(87) PCT Pub. No.: WO03/087341
PCT Pub. Date: Oct. 23, 2003

(65) Prior Publication Data
US 2005/0208489 A1    Sep. 22, 2005
US 2011/0014601 A2    Jan. 20, 2011

Related U.S. Application Data

(60) Provisional application No. 60/351,035, filed on Jan. 23, 2002.

(51) Int. Cl.
*C12N 15/82* (2006.01)
(52) U.S. Cl. ........................ 800/288; 435/468
(58) Field of Classification Search .................. None
See application file for complete search history.

(56) References Cited

U.S. PATENT DOCUMENTS

| | | | |
|---|---|---|---|
| 4,665,184 A | 5/1987 | Dervan et al. | |
| 4,795,700 A | 1/1989 | Dervan et al. | |
| 4,942,227 A | 7/1990 | Dervan et al. | |
| 5,356,802 A | 10/1994 | Chandrasegaran et al. | |
| 5,436,150 A | 7/1995 | Chandrasegaran et al. | |
| 5,487,994 A | 1/1996 | Chandrasegaran et al. | |
| 5,789,155 A | 8/1998 | Dervan et al. | |
| 5,789,538 A | 8/1998 | Rebar et al. | |
| 5,792,640 A | 8/1998 | Chandrasegaran et al. | |
| 5,916,794 A | 6/1999 | Chandrasegaran et al. | |
| 5,945,577 A | 8/1999 | Stice et al. | |
| 5,955,341 A | 9/1999 | Kang et al. | |
| 6,007,988 A | 12/1999 | Choo et al. | |
| 6,013,453 A | 1/2000 | Choo et al. | |
| 6,077,710 A | 6/2000 | Susko-Parrish et al. | |
| 6,140,081 A | 10/2000 | Barbas | |
| 6,140,466 A | 10/2000 | Barbas et al. | |
| 6,147,276 A | 11/2000 | Campbell et al. | |
| 6,242,568 B1 | 6/2001 | Barbas et al. | |
| 6,265,196 B1 | 7/2001 | Chandrasegaran et al. | |
| 6,326,166 B1 | 12/2001 | Pomerantz et al. | |
| 6,331,658 B1 | 12/2001 | Cooper et al. | |
| 6,453,242 B1 | 9/2002 | Eisenberg et al. | |
| 6,479,626 B1 | 11/2002 | Kim et al. | |
| 6,534,261 B1 | 3/2003 | Cox et al. | |
| 7,151,201 B2 * | 12/2006 | Barbas et al. | ............. 800/278 |
| 2002/0022021 A1 | 2/2002 | Emerson | |
| 2002/0107214 A1 | 8/2002 | Choulika et al. | |
| 2002/0110898 A1 | 8/2002 | Choulika et al. | |
| 2002/0152488 A1 | 10/2002 | Cooper et al. | |
| 2003/0131365 A1 | 7/2003 | Cooper et al. | |
| 2003/0232410 A1 | 12/2003 | Liljedahl et al. | |
| 2004/0019002 A1 | 1/2004 | Choulika et al. | |
| 2004/0121357 A1 | 6/2004 | Franklin | |

FOREIGN PATENT DOCUMENTS

| | | |
|---|---|---|
| EP | 0 957 165 | 11/1999 |
| WO | WO 95/09233 | 4/1995 |
| WO | WO 96/40882 | 12/1996 |
| WO | WO 97/47758 | 12/1997 |
| WO | WO 98/53058 | 11/1998 |
| WO | WO 98/53059 | 11/1998 |
| WO | WO 98/53060 | 11/1998 |
| WO | WO 00/09755 | 2/2000 |
| WO | WO 00/28008 | 5/2000 |
| WO | WO 00/42219 | 7/2000 |
| WO | WO 00/46385 | 8/2000 |
| WO | WO 00/46386 | 8/2000 |
| WO | WO 00/63365 | 10/2000 |
| WO | WO 01/05961 | 1/2001 |
| WO | WO 01/19981 | 3/2001 |

(Continued)

OTHER PUBLICATIONS

Bibikova M. et al. Stimulation of homologous recombination through targeted cleavage by chimeric nucleases. Mol Cell Biol. Jan. 2001;21(1):289-97.*
Wheeler G.N. et al. Inducible gene expression in transgenic Xenopus embryos. Curr Biol. Jul. 13, 2000;10(14):849-52.*
Hanin M. et al. Plant genome modification by plant homologous recombination. Curr Opin Plant Biol. Apr. 2003;6(2):157-62. Review.*
Britt A.B. et al. Re-engineering plant gene targeting. Trends Plant Sci. Feb. 2003;8(2):90-5. Review.*
Abremski K, Hoess R. Bacteriophage P1 site-specific recombination. Purification and properties of the Cre recombinase protein. J Biol Chem. Feb. 10, 1984;259(3):1509-14.

(Continued)

*Primary Examiner* — Cynthia Collins
(74) *Attorney, Agent, or Firm* — Ballard Spahr LLP

(57) ABSTRACT

The present invention provides for a method or methods of targeted genetic recombination or mutagenesis in a host cell or organism, and compositions useful for carrying out the method. The targeting method of the present invention exploits endogenous cellular mechanisms for homologous recombination and repair of double stranded breaks in genetic material. The present invention provides numerous improvements over previous mutagenesis methods, such advantages include that the method is generally applicable to a wide variety of organisms, the method is targeted so that the disadvantages associated with random insertion of DNA in-to host genetic material are eliminated, and certain embodiments require relatively little manipulation of the host genetic material for success. Additionally, it provides a method that produces organisms with specific gene modifications in a short period of time.

39 Claims, No Drawings

FOREIGN PATENT DOCUMENTS

| | | |
|---|---|---|
| WO | WO 01/40798 | 6/2001 |
| WO | WO 01/66717 | 9/2001 |
| WO | WO 02/04488 | 1/2002 |
| WO | WO 03/080809 | 10/2003 |
| WO | WO 03/087341 | 10/2003 |

OTHER PUBLICATIONS

Adams, et al. The genome sequence of *Drosophila melanogaster*. Science. Mar. 24, 2000;287(5461):2185-95.

Aggarwal et al. Novel site-specific DNA endonucleases. Curr Opin Struct Biol. Feb. 1998;8(1):19-25.

Akopian A, He J, Boocock MR, Stark WM. Chimeric recombinases with designed DNA sequence recognition. Proc Natl Acad Sci U S A. Jul. 22, 2003;100(15):8688-91.

Baubonis W, Sauer B. Genomic targeting with purified Cre recombinase. Nucleic Acids Res. May 11, 1993;21(9):2025-9.

BDGP Pattern Search: http://www.fruitfly.org/seq_tools/patscan.deleted/patscan.html, Dec. 21, 2005.

Beall EL, Rio DC. Drosophila IRBP/Ku p70 corresponds to the mutagen-sensitive mus309 gene and is involved in P-element excision in vivo. Genes Dev. Apr. 15, 1996;10(8):921-33.

Beerli RR, Barbas CF 3rd. Engineering polydactyl zinc-finger transcription factors. Nat Biotechnol. Feb. 2002;20(2):135-41.

Beerli RR, Segal DJ, Dreier B, Barbas CF 3rd. Toward controlling gene expression at will: specific regulation of the erbB-2/HER-2 promoter by using polydactyl zinc finger proteins constructed from modular building blocks. Proc Natl Acad Sci U S A. Dec. 8, 1998;95(25):14628-33.

Bibikova M, Beumer K, Trautman JK, Carroll D. Enhancing gene targeting with designed zinc finger nucleases. Science. May 2, 2003;300(5620):764.

Bitinaite J, Wah DA, Aggarwal AK, Schildkraut I. FokI dimerization is required for DNA cleavage. Proc Natl Acad Sci U S A. Sep. 1, 1998;95(18):10570-5.

Brenneman M, Gimble FS, Wilson JH. Stimulation of intrachromosomal homologous recombination in human cells by electroporation with site-specific endonucleases. Proc Natl Acad Sci U S A. Apr. 16, 1996;93(8):3608-12.

Brisson, et al., Expression of a bacterial gene in plants by using a viral vector. Nature 1984 310:511-514.

Broglie R, Coruzzi G, Fraley RT, Rogers SG, Horsch RB, Niedermeyer JG, Fink CL, Chua NH. Light-regulated expression of a pea ribulose-1,5-bisphosphate carboxylase small subunit gene in transformed plant cells. Science. May 25, 1984;224(4651):838-43.

Campbell,K.H.S., McWhir,J., Ritchie,W.A. and Wilmut,I (1996) Nature 380, 64-66.

Capecchi MR. Altering the genome by homologous recombination. Science. Jun. 16, 1989;244(4910):1288-92.

Carroll D, Segal DJ. Induced recombination in model systems. Curr. Res. Mol. Therap. 1(8):593-8.

Chandrasegaran S, Smith J. Chimeric restriction enzymes: what is next? Biol Chem. Jul.-Aug. 1999;380(7-8):841-8.

Chevalier BS, Kortemme T, Chadsey MS, Baker D, Monnat RJ, Stoddard BL. Design, activity, and structure of a highly specific artificial endonuclease. Mol Cell. Oct. 2002;10(4):895-905.

Choo Y, Sanchez-Garcia I, Klug A. In vivo repression by a site-specific DNA-binding protein designed against an oncogenic sequence. Nature. Dec. 15, 1994;372(6507):642-5.

Choulika A, Perrin A, Dujon B, Nicolas JF. Induction of homologous recombination in mammalian chromosomes by using the I-SceI system of *Saccharomyces cerevisiae*. Mol Cell Biol. Apr. 1995;15(4):1968-73.

Clough SJ, Bent AF. Floral dip: a simplified method for Agrobacterium-mediated transformation of *Arabidopsis thaliana*. Plant J. Dec. 1998;16(6):735-43.

Cohen-Tannoudji M, Robine S, Choulika A, Pinto D, El Marjou F, Babinet C, Louvard D, Jaisser F. I-SceI-induced gene replacement at a natural locus in embryonic stem cells. Mol Cell Biol. Mar. 1998;18(3):1444-8.

Cole-Strauss A, Yoon K, Xiang Y, Byrne BC, Rice MC, Gryn J, Holloman WK, Kmiec EB. Correction of the mutation responsible for sickle cell anemia by an RNA-DNA oligonucleotide. Science. Sep. 6, 1996;273(5280):1386-9.

Coruzzi G, Broglie R, Edwards C, Chua NH. Tissue-specific and light-regulated expression of a pea nuclear gene encoding the small subunit of ribulose-1,5-bisphosphate carboxylase. EMBO J. Aug. 1984;3(8):1671-9.

Desjarlais JR, Berg JM. Toward rules relating zinc finger protein sequences and DNA binding site preferences. Proc Natl Acad Sci U S A. Aug. 15, 1992;89(16):7345-9.

Desjarlais JR, Berg JM. Use of a zinc-finger consensus sequence framework and specificity rules to design specific DNA binding proteins. Proc Natl Acad Sci U S A. Mar. 15, 1993;90(6):2256-60.

Disruption of the proto-oncogene int-2 in mouse embryo-derived stem cells: a general strategy for targeting mutations to non-selectable genes. Nature. Nov. 24, 1988;336(6197):348-52.

Donoho G, Jasin M, Berg P. Analysis of gene targeting and intrachromosomal homologous recombination stimulated by genomic double-strand breaks in mouse embryonic stem cells. Mol Cell Biol. Jul. 1998;18(7):4070-8.

Dray T, Gloor GB. Homology requirements for targeting heterologous sequences during P-induced gap repair in *Drosophila melanogaster*. Genetics. Oct. 1997;147(2):689-99.

Dreier B, Beerli RR, Segal DJ, Flippin JD, Barbas CF 3rd.. Development of zinc finger domains for recognition of the 5'-ANN-3' family of DNA sequences and their use in the construction of artificial transcription factors. J Biol Chem. Aug. 3, 2001;276(31):29466-78.

Dreier B, Segal DJ, Barbas CF 3rd. Insights into the molecular recognition of the 5'-GNN-3' family of DNA sequences by zinc finger domains. J Mol Biol. Nov. 3, 2000;303(4):489-502.

Elliott B, Richardson C, Winderbaum J, Nickoloff JA, Jasin M. Gene conversion tracts from double-strand break repair in mammalian cells. Mol Cell Biol. Jan. 1998;18(1):93-101.

Elrod-Erickson M, Pabo CO. Binding studies with mutants of Zif268. Contribution of individual side chains to binding affinity and specificity in the Zif268 zinc finger-DNA complex. J Biol Chem. Jul. 2, 1999;274(27):19281-5.

Engels WR, Johnson-Schlitz DM, Eggleston WB, Sved J. High-frequency P element loss in Drosophila is homolog dependent. Cell. Aug. 10, 1990;62(3):515-25.

Engels WR. Reversal of fortune for Drosophila geneticists? Science. Jun. 16, 2000;288(5473):1973-5.

Evans MJ, Kaufman MH. Establishment in culture of pluripotential cells from mouse embryos. Nature. Jul. 9, 1981;292(5819):154-6.

Ferguson-Smith AC, Surani MA. Imprinting and the epigenetic asymmetry between parental genomes. Science. Aug. 10, 2001;293(5532):1086-9.

Galway ME, Masucci JD, Lloyd AM, Walbot V, Davis RW, Schiefelbein JW. The TTG gene is required to specify epidermal cell fate and cell patterning in the Arabidopsis root. Dev Biol. Dec. 1994;166(2):740-54.

GenBank No. AJ133743. Jan. 26, 2001.

GenBank No. F20055, Mar. 6, 1996.

GenBank No. F20056, Mar. 6, 1996.

Geyer PK, Corces VG. Separate regulatory elements are responsible for the complex pattern of tissue-specific and developmental transcription of the yellow locus in *Drosophila melanogaster*. Genes Dev. Nov. 1987;1(9):996-1004.

Gloor GB, Moretti J, Mouyal J, Keeler KJ. Distinct P-element excision products in somatic and germline cells of *Drosophila melanogaster*. Genetics. Aug. 2000;155(4):1821-30.

Gloor GB, Nassif NA, Johnson-Schlitz DM, Preston CR, Engels WR. Targeted gene replacement in Drosophila via P element-induced gap repair. Science. Sep. 6, 1991;253(5024):1110-7.

Gorlich D, Mattaj IW. Nucleocytoplasmic transport. Science. Mar. 15, 1996;271(5255):1513-8.

Gowda S, Wu FC, Sheperd RJ Identification of promoter sequences for the major RNA transcripts of figwort mosaic and peanut chlorotic streak viruses (caulimovirus group). 1989 J. Cell Biology. 13D:301.

Greisman HA, Pabo CO. A general strategy for selecting high-affinity zinc finger proteins for diverse DNA target sites. Science. Jan. 31, 1997;275(5300):657-61.

Gu H, Marth JD, Orban PC, Mossmann H, Rajewsky K. Deletion of a DNA polymerase beta gene segment in T cells using cell type-specific gene targeting. Science. Jul. 1, 1994;265(5168):103-6.

Gu H, Zou YR, Rajewsky K. Independent control of immunoglobulin switch recombination at individual switch regions evidenced through Cre-loxP-mediated gene targeting. Cell. Jun. 18, 1993;73(6):1155-64.

Gurley WB, Czarnecka E, Nagao RT, Key JL. Upstream sequences required for efficient expression of a soybean heat shock gene. Mol Cell Biol. Feb. 1986;6(2):559-65.

Hanson KD, Sedivy JM. Analysis of biological selections for high-efficiency gene targeting. Mol Cell Biol. Jan. 1995;15(1):45-51.

Havre PA, Glazer PM. Targeted mutagenesis of simian virus 40 DNA mediated by a triple helix-forming oligonucleotide. J Virol. Dec. 1993;67(12):7324-31.

Hicks GR, Smith HM, Shieh M, Raikhel NV. Three classes of nuclear import signals bind to plant nuclei. Plant Physiol. Apr. 1995;107(4):1055-8.

Huang B, Schaeffer CJ, Li Q, Tsai MD. Splase: a new class IIS zinc-finger restriction endonuclease with specificity for Sp1 binding sites. J Protein Chem. Jul. 1996;15(5):481-9.

Isalan M, Choo Y, Klug A. Synergy between adjacent zinc fingers in sequence-specific DNA recognition. Proc Natl Acad Sci U S A. May 27, 1997;94(11):5617-21.

Isalan M, Klug A, Choo Y. A rapid, generally applicable method to engineer zinc fingers illustrated by targeting the HIV-1 promoter. Nat Biotechnol. Jul. 2001;19(7):656-60.

Isalan M, Klug A, Choo Y. Comprehensive DNA recognition through concerted interactions from adjacent zinc fingers. Biochemistry. Sep. 1, 1998;37(35):12026-33.

Jaenisch R. Science. Jun. 10, 1988;240(4858):1468-74.

Jallepalli PV, Waizenegger IC, Bunz F, Langer S, Speicher MR, Peters JM, Kinzler KW, Vogelstein B, Lengauer C. Securin is required for chromosomal stability in human cells. Cell. May 18, 2001;105(4):445-57.

Jasin M. Genetic manipulation of genomes with rare-cutting endonucleases. Trends Genet. Jun. 1996;12(6):224-8.

Jeggo PA. DNA breakage and repair. Adv Genet. 1998;38:185-218.

Johnson RD, Jasin M. Double-strand-break-induced homologous recombination in mammalian cells. Biochem Soc Trans. May, 2001;29(Pt 2):196-201.

Keeler KJ, Dray T, Penney JE, Gloor GB. Gene targeting of a plasmid-borne sequence to a double-strand DNA break in Drosophila melanogaster. Mol Cell Biol. Feb. 1996;16(2):522-8.

Khanna KK, Jackson SP. DNA double-strand breaks: signaling, repair and the cancer connection. Nat Genet. Mar. 2001;27(3):247-54.

Kim JS, Pabo CO. Getting a handhold on DNA: design of poly-zinc finger proteins with femtomolar dissociation constants. Proc Natl Acad Sci U S A. Mar. 17, 1998;95(6):2812-7.

Kim YG, Chandrasegaran S. Chimeric restriction endonuclease. Proc Natl Acad Sci U S A. Feb. 1, 1994;91(3):883-7.

Kim YG, Li L, Chandrasegaran S Insertion and deletion mutants of FokI restriction endonuclease. J. Biol Chem. Dec. 16, 1994;269(50):31978-82.

Kim YG et al. Construction of a Z-DNA-specific restriction endonuclease. Proc Nati Acad Sci U S A. Nov. 25, 1997;94(24):12875-9.

Kim YG, Smith J, Durgesha M, Chandrasegaran S. Chimeric restriction enzyme: Gal4 fusion to FokI cleavage domain. Biol Chem. Apr.-May, 1998;379(4-5):489-95.

Klein et al. High-velocity microprojectiles for delivering nucleic acids into living cells 1987 Nature 327:70-3.

Klein TM, Arentzen R, Lewis PA, Fitzpatrick-McElligott S. Transformation of microbes, plants and animals by particle bombardment. Biotechnology (N Y). Mar. 1992;10(3):286-91.

Koller BH, Smithies O. Altering genes in animals by gene targeting. Annu Rev Immunol. 1992;10:705-30.

Kuehn MR, Bradley A, Robertson EJ, Evans MJ. A potential animal model for Lesch-Nyhan syndrome through introduction of HPRT mutations into mice. Nature. Mar. 19-25, 1987;326(6110):295-8.

Lai L, Kolber-Simonds D, Park KW, Cheong HT, Greenstein JL, Im GS, Samuel M, Bonk A, Rieke A, Day BN, Murphy CN, Carter DB, Hawley RJ, Prather RS. Production of alpha-1,3-galactosyltransferase knockout pigs by nuclear transfer cloning. Science. Feb. 8, 2002;295(5557):1089-92.

Li L, Chandrasegaran S. Alteration of the cleavage distance of Fok I restriction endonuclease by insertion mutagenesis. Proc Natl Acad Sci U S A. Apr. 1, 1993;90(7):2764-8.

Lin L, Wu LP, Chandrasegaran S. Functional domains in Fok I restriction endonuclease. Proc Natl Acad Sci U S A. May 15, 1992;89(10):4275-9.

Liu PQ, Rebar EJ, Zhang L, Liu Q, Jamieson AC, Liang Y, Qi H, Li PX, Chen B, Mendel MC, Zhong X, Lee YL, Eisenberg SP, Spratt SK, Case CC, Wolfe AP. Regulation of an endogenous locus using a panel of designed zinc finger proteins targeted to accessible chromatin regions. Activation of vascular endothelial growth factor A. J Biol Chem. Apr. 6, 2001;276(14):11323-34.

Liu Q, Segal DJ, Ghiara JB, Barbas CF 3rd. Design of polydactyl zinc-finger proteins for unique addressing within complex genomes. Proc Natl Acad Sci U S A. May 27, 1997;94(11):5525-30.

Liu Q, Xia Z, Zhong X, Case CC. Validated zinc finger protein designs for all 16 GNN DNA triplet targets. J Biol Chem. Feb. 8, 2002;277(6):3850-6.

Mattaj IW, Englmeier L. Nucleocytoplasmic transport: the soluble phase. Annu Rev Biochem. 1998;67:265-306.

McCreath KJ, Howcroft J, Campbell KH, Colman A, Schnieke AE, Kind AJ. Production of gene-targeted sheep by nuclear transfer from cultured somatic cells. Nature. Jun. 29, 2000;405(6790):1066-9.

Mismer D, Rubin GM. Analysis of the promoter of the ninaE opsin gene in *Drosophila melanogaster*. Genetics. Aug. 1987;116(4):565-78.

Moore M, Choo Y, Klug A. Design of polyzinc finger peptides with structured linkers. Proc Natl Acad Sci U S A. Feb. 13, 2001;98(4):1432-6.

Nahon E, Raveh D. Targeting a truncated Ho-endonuclease of yeast to novel DNA sites with foreign zinc fingers. Nucleic Acids Res. Mar. 1, 1998;26(5):1233-9.

Odell JT, Nagy F, Chua NH. Identification of DNA sequences required for activity of the cauliflower mosaic virus 35S promoter. Nature. Feb. 28-Mar. 6, 1985;313(6005):810-2.

Pabo CO, Peisach E, Grant RA. Design and selection of novel Cys2His2 zinc finger proteins. Annu Rev Biochem. 2001;70:313-40.

Pavletich NP, Pabo CO. Zinc finger-DNA recognition: crystal structure of a Zif268-DNA complex at 2.1 A. Science. May 10, 1991;252(5007):809-17.

Pelletier MK, Shirley BW. Analysis of flavanone 3-hydroxylase in Arabidopsis seedlings. Coordinate regulation with chalcone synthase and chalcone isomerase. Plant Physiol. May 1996;111(1):339-45.

Petersen RB, Lindquist S. Regulation of HSP70 synthesis by messenger RNA degradation. Cell Regul. Nov. 1989;1(1):1 35-49.

Polejaeva IA, Chen SH, Vaught TD, Page RL, Mullins J, Ball S, Dai Y, Boone J, Walker S, Ayares DL, Colman A, Campbell KH. Cloned pigs produced by nuclear transfer from adult somatic cells. Nature. Sep. 7, 2000;407(6800):86-90.

Porteus MH, Baltimore D. Chimeric nucleases stimulate gene targeting in human cells. Science. May 2, 2003;300(5620):763.

Porteus MH, Cathomen T, Weitzman MD, Baltimore D. Efficient gene targeting mediated by adeno-associated virus and DNA double-strand breaks. Mol Cell Biol. May 2003;23(10):3558-65.

Preston CR, Sved JA, Engels WR. Flanking duplications and deletions associated with P-induced male recombination in Drosophila. Genetics. Dec. 1996;144(4):1623-38.

Puchta H, Dujon B, Hohn B. Homologous recombination in plant cells is enhanced by in vivo induction of double strand breaks into DNA by a site-specific endonuclease. Nucleic Acids Res. Nov. 11, 1993;21(22):5034-40.

Rebar EJ, Pabo CO. Zinc finger phage: affinity selection of fingers with new DNA-binding specificities. Science. Feb. 4, 1994;263(5147):671-3.

Rideout WM 3rd, Eggan K, Jaenisch R. Nuclear cloning and epigenetic reprogramming of the genome. Science. Aug. 10, 2001;293(5532):1093-8.

Rong YS, Golic KG. A targeted gene knockout in Drosophila. Genetics. Mar. 2001;157(3):1307-12.

Rong YS, Golic KG. Gene targeting by homologous recombination in Drosophila. Science. Jun. 16, 2000;288(5473):2013-8.

Rothstein RJ. One-step gene disruption in yeast. Methods Enzymol. 1983;101:202-11.

Rouet P, Smih F, Jasin M. Expression of a site-specific endonuclease stimulates homologous recombination in mammalian cells. Proc Natl Acad Sci U S A. Jun. 21, 1994;91(13):6064-8.

Rouet P, Smih F, Jasin M. Introduction of double-strand breaks into the genome of mouse cells by expression of a rare-cutting endonuclease. Mol Cell Biol. Dec. 1994;14(12):8096-106.

Sandford JC, Devit MJ, Russell JA, Smith FD, Harpending PR, Roy MK, Johnston SA. An improved, helium-driven biolistic device. Technique-A Journal of Methods in Cell and Molecular Biology. 1991;3:3-16.

Sargent RG, Brenneman MA, Wilson JH. Repair of site-specific double-strand breaks in a mammalian chromosome by homologous and illegitimate recombination. Mol Cell Biol. Jan. 1997;17(1):267-77.

Schnieke AE, Kind AJ, Ritchie WA, Mycock K, Scott AR, Ritchie M, Wilmut I, Colman A, Campbell KH. Human factor IX transgenic sheep produced by transfer of nuclei from transfected fetal fibroblasts. Science. Dec. 19, 1997;278(5346):2130-3.

Sedivy JM, Sharp PA. Positive genetic selection for gene disruption in mammalian cells by homologous recombination. Proc Natl Acad Sci U S A. Jan. 1989;86(1):227-31.

Segal DJ, Carroll D. Endonuclease-induced, targeted homologous extrachromosomal recombination in Xenopus oocytes. Proc Natl Acad Sci U S A. Jan. 31, 1995;92(3):806-10.

Segal DJ, Dreier B, Beerli RR, Barbas CF 3rd. Toward controlling gene expression at will: selection and design of zinc finger domains recognizing each of the 5'-GNN-3' DNA target sequences. Proc Natl Acad Sci U S A. Mar. 16, 1999;96(6):2758-63.

Segal DJ. The use of zinc finger peptides to study the role of specific factor binding sites in the chromatin environment. Methods. Jan. 2002;26(1):76-83.

Sera T, Uranga C. Rational design of artificial zinc-finger proteins using a nondegenerate recognition code table. Biochemistry. Jun. 4, 2002;41(22):7074-81.

Severin K, Schoffl F. Heat-inducible hygromycin resistance in transgenic tobacco. Plant Mol Biol. Dec. 1990;15(6):827-33.

Shi Y, Berg JM. Specific DNA-RNA hybrid binding by zinc finger proteins. Science. Apr. 14, 1995;268(5208):282-4.

Shillito et al (1988) Plant.Mol.Bio. A Prac.App.(Shaw, Ed. IRL Press)pp. 161-186.

Shin T, Kraemer D, Pryor J, Liu L, Rugila J, Howe L, Buck S, Murphy K, Lyons L, Westhusin M. A cat cloned by nuclear transplantation. Nature. Feb. 21, 2002;415(6874):859.

Shirley BW, Kubasek WL, Storz G, Bruggemann E, Koornneef M, Ausubel FM, Goodman HM. Analysis of Arabidopsis mutants deficient in flavonoid biosynthesis. Plant J. Nov. 1995;8(5):659-71.

Smih F, Rouet P, Romanienko PJ, Jasin M. Double-strand breaks at the target locus stimulate gene targeting in embryonic stem cells. Nucleic Acids Res. Dec. 25, 1995;23(24):5012-9.

Smith J, Berg JM, Chandrasegaran S. A detailed study of the substrate specificity of a chimeric restriction enzyme. Nucleic Acids Res. Jan. 15, 1999;27(2):674-81.

Smith J, Bibikova M, Whitby FG, Reddy AR, Chandrasegaran S, Carroll D. Requirements for double-strand cleavage by chimeric restriction enzymes with zinc finger DNA-recognition domains. Nucleic Acids Res. Sep. 1, 2000;28(17):3361-9.

Staveley BE, Heslip TR, Hodgetts RB, Bell JB. Protected P-element termini suggest a role for inverted-repeat-binding protein in transposase-induced gap repair in *Drosophila melanogaster*. Genetics. Mar. 1995;139(3):1321-9.

Sternberg N, Hamilton D, Hoess R. Bacteriophage P1 site-specific recombination. II. Recombination between loxP and the bacterial chromosome. J Mol Biol. Aug. 25, 1981;150(4):487-507.

Taghian DG, Nickoloff JA. Chromosomal double-strand breaks induce gene conversion at high frequency in mammalian cells. Mol Cell Biol. Nov. 1997;17(11):6386-93.

Takamatsu N, Ishikawa M, Meshi T, Okada Y. Expression of bacterial chloramphenicol acetyltransferase gene in tobacco plants mediated by TMV-RNA. EMBO J. Feb. 1987;6(2):307-11.

Takasu-Ishikawa E, Yoshihara M, Hotta Y. Extra sequences found at P element excision sites in *Drosophila melanogaster*. Mol Gen Genet. Mar. 1992;232(1):17-23.

Thierry A, Perrin A, Boyer J, Fairhead C, Dujon B, Frey B, Schmitz G. Cleavage of yeast and bacteriophage T7 genomes at a single site using the rare cutter endonuclease I-Sce I. Nucleic Acids Res. Jan. 11, 1991;19(1):189-90.

Urnov FD, Miller JC, Lee YL, Beausejour CM, Rock JM, Augustus S, Jamieson AC, Porteus MH, Gregory PD, Holmes MC. Highly efficient endogenous human gene correction using designed zinc-finger nucleases. Nature. Jun. 2, 2005;435(7042):646-51.

van Gent DC, Hoeijmakers JH, Kanaar R. Chromosomal stability and the DNA double-stranded break connection. Nat Rev Genet. Mar. 2001;2(3):196-206.

Vasquez KM, Marburger K, Intody Z, Wilson JH. Manipulating the mammalian genome by homologous recombination. Proc Natl Acad Sci U S A. Jul. 17, 2001;98(15):8403-10.

Velten, J., Velten, L., Hain, R. & Schell, J. Isolation of a Dual Plant Promoter Fragment From the Ti Plasmid of Agrobacterium-Tumefaciens 1984 EMBO J. 3, 2723-2730.

Wah DA, Hirsch JA, Dorner LF, Schildkraut I, Aggarwal AK. Structure of the multimodular endonuclease FokI bound to DNA. Nature. Jul. 3, 1997;388(6637):97-100.

Walker AR, Davison PA, Bolognesi-Winfield AC, James CM, Srinivasan N, Blundell TL, Esch JJ, Marks MD, Gray JC. The Transparent Testa GLABRA1 locus, which regulates trichome differentiation and anthocyanin biosynthesis in Arabidopsis, encodes a WD40 repeat protein. Plant Cell. Jul. 1999;11(7):1337-50.

Wang G, Levy DD, Seidman MM, Glazer PM. Targeted mutagenesis in mammalian cells mediated by intracellular triple helix formation. Mol Cell Biol. Mar. 1995;15(3):1759-68.

Wang G, Seidman MM, Glazer PM. Mutagenesis in mammalian cells induced by triple helix formation and transcription-coupled repair. Science. Feb. 9, 1996;271(5250):802-5.

Wilmut I, Schnieke AE, McWhir J, Kind AJ, Campbell KH. Viable offspring derived from fetal and adult mammalian cells. Nature. Feb. 27, 1997;385(6619):810-3.

Wilson JH. Pointing fingers at the limiting step in gene targeting. Nat Biotechnol. Jul. 2003;21(7):759-60.

Wolfe SA, Grant RA, Elrod-Erickson M, Pabo CO. Beyond the "recognition code": structures of two Cys2His2 zinc finger/TATA box complexes. Structure (Camb). Aug. 2001;9(8):717-23.

Wolfe SA, Nekludova L, Pabo CO. DNA recognition by Cys2His2 zinc finger proteins. Annu Rev Biophys Biomol Struct. 2000;29:183-212.

Xu L, Zerby D, Huang Y, Ji H, Nyanguile OF, de los Angeles JE, Kadan MJ. A versatile framework for the design of ligand-dependent, transgene-specific transcription factors. Mol Ther. Feb. 2001;3(2):262-73.

Yanez RJ, Porter AC. Therapeutic gene targeting. Gene Ther. Feb. 1998;5(2):149-59.

Zhang L, Spratt SK, Liu Q, Johnstone B, Qi H, Raschke EE, Jamieson AC, Rebar EJ, Wolffe AP, Case CC. Synthetic zinc finger transcription factor action at an endogenous chromosomal site. Activation of the human erythropoietin gene. J Biol Chem. Oct. 27, 2000;275(43):33850-60.

Zufferey R, Donello JE, Trono D, Hope TJ. Woodchuck hepatitis virus posttranscriptional regulatory element enhances expression of transgenes delivered by retroviral vectors. J Virol. Apr. 1999;73(4):2886-92.

Bibikova et al., "Stimulation of Homologous Recombination Through Targeted Cleavage by Chimeric Nucleases," *Mol. & Cell. Biology*, 21(1):289-297 (Jan. 2001).

Bibikova et al., "Targeted Chromosomal Cleavage and Mutagenesis in Drosophila Using Zinc-Finger Nucleases," *Genetics*, 161(3):1169-1175 (Jul. 2002).

Jeggo, P.A., "Identification of Genes Involved in Repair of DNA Double-Strand Breakds in Mammalian Cells," *Radiation Research*, 150(5):S80-S90 (1998).

Kim et al., "Hybrid Restriction Enzymes: Zinc Finger Fusions to Fok I Cleavage Domain," *Proc. Natl. Sci. USA*, 93(3):1156-1160 (Feb. 1996).

Examiner's First Report dated Dec. 9, 2005 (Australian Application No. 2003251286).
First Statement of Proposed Amendments dated Oct. 10, 2006 (Australian Application No. 2003251286).
Withdrawal of Postponement of Acceptance dated Aug. 3, 2007 (Australian Application No. 2003251286).
Notice of Acceptance dated Aug. 7, 2007 (Australian Application No. 2003251286).
Notice of Sealing dated Nov. 29, 2007 (Australian Application No. 2003251286).
Voluntary Amendments dated Jul. 23, 2004 (Canadian Application No. 2,474,486).
Examiner's Requisition dated Jan. 6, 2005 (Canadian Application No. 2,474,486).
Response to Examiner's Report dated Jul. 5, 2005 (Canadian Application No. 2,474,486).
Examiner's Requisition dated May 26, 2008 (Canadian Application No. 2,474,486).
Response to Examiner's Requisition under Rule 30(2) dated Nov. 26, 2008 (Canadian Application No. 2,474,486).
Examiner's Requisition dated May 17, 2010 (Canadian Application No. 2,474,486).
International Search Report for WO 2003/087341 dated Mar. 15, 2004 (PCT/US03/02012).
Written Opinion for WO 2003/087341 dated Jun. 17, 2004 (PCT/US03/02012).
International Preliminary Examination Report for WO 2003/087341 dated Oct. 28, 2004 (PCT/US03/02012).
Supplementary European Search Report dated Jun. 30, 2005 (EP Application No. 03746527.5).
Communication pursuant to Article 96(2) EPC dated Sep. 23, 2005 (EP Application No. 03746527.5).
Response to Examination Report dated Jan. 26, 2006 (EP Application No. 03746527.5).
Supplemental Response to Examination Report dated Mar. 30, 2006 (EP Application No. 03746527.5).
Communication under Rule 51(4) EPC dated Jun. 8, 2006 (EP Application No. 03746527.5).
Decision to grant a European patent pursuant to article 97(2) EPC dated Nov. 9, 2006 (EP Application No. 03746527.5).
Communication regarding the expiry of the time limit within which notice of opposition may be filed dated Oct. 10, 2007 (EP Application No. 03746527.5).
Notification of First Office Action dated Oct. 21, 2005 (CN Application No. 03802664.3).
Notification of Second Office Action dated Dec. 5, 2008 (CN Application No. 03802664.3).
Third Notification of Examiner's Opinion dated Jun. 5, 2009 (CN Application No. 03802664.3).
Notification for Go Through the Formalities of Registration dated Sep. 4, 2009 (CN Application No. 03802664.3).
Certificate of Invention Patent dated Dec. 30, 2009 (CN Application No. 03802664.3).
Notice of Reasons for Rejection dated Mar. 10, 2009 (JP Application No. 2003-584285).
Response to Rejection dated Jun. 10, 2009 (JP Application No. 2003-584285).
Notice of Reasons for Rejection dated Jun. 30, 2010 (JP Application No. 2003-584285).
Jasin M. (2000) Chromosome breaks and genomic instability. Cancer Invest., 18(1): 78-86.
Liang F, Han M, Romanienko PJ, Jasin M. (1998) Homology-directed repair is a major double-strand break repair pathway in mammalian cells. Proc Natl Acad Sci USA, 95(9): 5172-5177.
Salomon S, Puchta H. (1998) Capture of genomic and T-DNA sequences during double-strand break repair in somatic plant cells. EMBO J., 17(20): 6086-6095.

* cited by examiner

SEQUENCE LISTING

```
<160> NUMBER OF SEQ ID NOS: 9

<210> SEQ ID NO 1
<211> LENGTH: 9
<212> TYPE: DNA
<213> ORGANISM: Artificial
<220> FEATURE:
<223> OTHER INFORMATION: Synthetic Primer

<400> SEQUENCE: 1 gcggatgcg                                                              9

<210> SEQ ID NO 2
<211> LENGTH: 9
<212> TYPE: DNA
<213> ORGANISM: Artificial
<220> FEATURE:
<223> OTHER INFORMATION: Synthetic Primer

<400> SEQUENCE: 2 gcggtagcg                                                              9
```

-continued

```
<210> SEQ ID NO 3
<211> LENGTH: 9
<212> TYPE: DNA
<213> ORGANISM: Drosophilia melanogaster

<400> SEQUENCE: 3 gtggatgag                                                                  9

<210> SEQ ID NO 4
<211> LENGTH: 9
<212> TYPE: DNA
<213> ORGANISM: Drosophila melanogaster

<400> SEQUENCE: 4 gcggtaggc                                                                  9

<210> SEQ ID NO 5
<211> LENGTH: 24
<212> TYPE: DNA
<213> ORGANISM: Artificial
<220> FEATURE:
<223> OTHER INFORMATION: Synthetic Primer

<400> SEQUENCE: 5
attccttgtg tccaaaataa tgac                                                24

<210> SEQ ID NO 6
<211> LENGTH: 23
<212> TYPE: DNA
<213> ORGANISM: Artificial
<220> FEATURE:
<223> OTHER INFORMATION: Synthetic Primer

<400> SEQUENCE: 6
aaaataggca tatgcatcat cgc                                                 23

<210> SEQ ID NO 7
<211> LENGTH: 25
<212> TYPE: DNA
<213> ORGANISM: Artificial
<220> FEATURE:
<223> OTHER INFORMATION: Synthetic Primer

<400> SEQUENCE: 7
attttgtaca tatgttctta agcag                                               25

<210> SEQ ID NO 8
<211> LENGTH: 24
<212> TYPE: DNA
<213> ORGANISM: Arabidopsis thaliana

<400> SEQUENCE: 8
tccggtcaca gaatcgccgt cgga                                                24

<210> SEQ ID NO 9
<211> LENGTH: 24
<212> TYPE: DNA
<213> ORGANISM: Arabidopsis thaliana

<400> SEQUENCE: 9
acttccttcg attggaacga tgta                                                24
```

TARGETED CHROMOSOMAL MUTAGENASIS USING ZINC FINGER NUCLEASES

CROSS REFERENCE TO RELATED APPLICATIONS

The present application is a National Phase Application of International Application No. PCT/US03/002012 filed on Jan. 22, 2003, which claims priority from U.S. Provisional Patent Application No. 60/351,035 filed Jan. 23, 2002, which is hereby incorporated herein by reference in its entirety.

ACKNOWLEDGMENT OF FEDERAL RESEARCH SUPPORT

The U.S. Government has certain rights in the invention based upon partial support by Grant RO1 GM 58504.

BACKGROUND OF THE INVENTION

Gene targeting—the process of gene replacement by homologous recombination or mutation—is a very useful, but typically inefficient technique for introducing desired changes in the genetic material of a host cell. Only when powerful selection for the targeted product can be applied is recovery of the desired alteration possible. A general method for improving the efficiency of gene targeting would be valuable in many circumstances, as would extension of this tool to a broader range of organisms.

It has been demonstrated in model experiments that introduction of a double-strand break (DSB) in host DNA greatly enhances the frequency of localized recombination. However, those tests required insertion of a recognition site for a specific endonuclease before cleavage could be induced. Similarly, in *Drosophila* the DSBs produced by P-element excision are recombinagenic, but require the P-element to preexist at the target site.

Although previously demonstrated methods of genetic transformation had been highly successful, transformation without targeted recombination has also been accompanied by problems associated with random insertion of the introduced DNA. Random integration can lead to the inactivation of essential genes, or to the aberrant expression of the introduced gene. Additional problems associated with genetic transformation include mosaicism due to multiple integrations, and technical difficulties associated with generation of replication defective recombinant viral vectors.

Targeted genetic recombination or mutation of a cell or organism is now possible because complete genomic sequences have been determined for a number of organisms, and more sequences are being obtained each day. Not only would the ability to direct a mutation to a specific genetic locus greatly aid those studying the function of particular genes, targeted genetic recombination would also have therapeutic and agricultural applications. Methods of targeted genetic recombination are needed that are more general, efficient, and/or reproducible than currently available techniques.

SUMMARY OF THE INVENTION

The present invention provides compositions and methods for carrying out targeted genetic recombination or mutation. Any segment of endogenous nucleic acid in a cell or organism can be modified by the method of the invention as long as the sequence of the target region, or portion of the target region, is known, or if isolated DNA homologous to the target region is available.

In certain embodiments, the compositions and methods comprise the transformation of a host organism by introducing a nucleic acid molecule encoding a chimeric zinc finger nuclease into a cell or organism and identifying a resulting cell or organism in which a selected endogenous DNA sequence is cleaved and exhibits a mutation.

In a preferred embodiment, such methods comprise selecting a zinc finger DNA binding domain capable of preferentially binding to a specific host DNA locus to be mutated; further selecting a non-specific DNA cleavage domain capable of cleaving double-stranded DNA when operatively linked to said binding domain and introduced into the host cell; further selecting an inducible promoter region capable of inducing expression in the host cell; and further operatively linking DNA encoding the binding domain and the cleavage domain and the inducible promoter region to produce a DNA construct. The DNA construct is then introduced into a target host cell and at least one host cell exhibiting recombination at the target locus in the host DNA is identified. In a particular embodiment, the DNA binding domain comprises the binding domains of three $Cis_2His_2$ zinc fingers. In another embodiment, the cleavage domain comprises a cleavage domain derived from the Type II restriction endonuclease FokI. In one embodiment, an inducible heat shock promoter is operatively linked to DNA encoding the chimeric zinc finger nuclease.

Additional embodiments involve methods for targeted insertion by homologous recombination of selected DNA sequences (donor DNA). Donor DNA can comprise a sequence that encodes a product to be produced in the host cell. Said product can be a product produced for the benefit of the host cell or organism (for example, gene therapy), or the product can be one that is produced for use outside the host cell or organism (for example, the product may be selected from, but not limited to, pharmaceuticals, hormones, protein products used in the manufacture of useful objects or devices, nutriceuticals, products used in chemical manufacture or synthesis, etc.).

In a certain embodiment, the present invention is utilized to disrupt a targeted gene in a somatic cell. Such gene may be over-expressed in one or more cell types resulting in disease. Disruption of such gene may only be successful in a low percentage of somatic cells but such disruption may contribute to better health for an individual suffering from disease due to over-expression of such gene.

In another embodiment, the present invention can be utilized to disrupt a targeted gene in a germ cell. Cells with such disruption in the targeted gene can be selected for in order to create an organism without function of the targeted gene. In such cell the targeted gene function can be completely knocked out.

In another embodiment, the present invention can be utilized to enhance expression of a particular gene by the insertion of a control element into a somatic cell. Such a control element may be selected from a group consisting of, but not limited to, a constitutively active, inducible, tissue-specific or development stage-specific promoters. Such control element may be targeted to a chromosomal locus where it will effect expression of a particular gene that is responsible for a product with a therapeutic effect in such a cell or the host organism. The present invention may further provide for the insertion of donor DNA containing a gene encoding a product that, when expressed, has a therapeutic effect on the host cell or organism. An example of such a therapeutic method would be to use the targeted genetic recombination of the present invention to effect insertion into a pancreatic cell of an active promoter operatively linked to donor DNA containing an insulin gene. The pancreatic cell containing the donor DNA would then produce insulin, thereby aiding a diabetic host. Additionally, donor DNA constructs could be inserted into a crop genome in order to effect the production of a pharmaceutically relevant gene product. A gene encoding a pharmaceutically useful protein product, such as insulin or hemoglobin, functionally linked to a control element, such as a constitutively active, inducible, tissue-specific or development stage-specific promoters, could be inserted into a host plant in order to produce a large amount of the pharmaceutically useful protein product in the host plant. Such protein products could then be isolated from the plant. Alternatively, the above-mentioned methods can be utilized in a germ cell.

The present invention can be utilized in both somatic and germ line cells to effect alteration at any chromosomal target locus.

Methods of the present invention are applicable to a wide range of cell types and organisms. The present invention can apply to any of the following cells, although the methods of the invention are not limited to the cells or organisms herein listed: A single celled or multicellular organism; an oocyte; a gamete; a germline cell in culture or in the host organism; a somatic cell in culture or in the host organism; to an insect cell, including an insect selected from the group consisting of *Coleoptera*, *Diptera*, *Hemiptera*, *Homoptera*, *Hymenoptera*, *Lepidoptera*, or *Orthoptera*, including a fruit fly, a mosquito and a medfly; a plant cell, including a monocotyledon cell and a dicotyledon cell; a mammalian cell, including but not limited to a cell selected from the group consisting of mouse, rat, pig, sheep, cow, dog or cat cells; an avian cell, including, but not limited to a cell selected from the group consisting of chicken, turkey, duck or goose cells; or a fish cell, including, but not limited to zebrafish, trout or salmon cells.

Many alterations and variations of the invention exist as described herein. The invention is exemplified for targeted genetic recombination in the insect, *Drosophila* and the plant, *Arabidopsis*. In *Drosophila* and *Arabidopsis*, the nucleotide sequence is known for most of the genome. Large segments of genomic sequences from other organisms are becoming known at a fast pace. The elements necessary to carry out the methods of the present invention as herein disclosed can be adapted for application in any cell or organism. The invention therefore provides a general method for targeted genetic recombination in any cell or organism.

Table I: Illustrates the number of germline mutants recovered by crossing males exposed to a heat shock with attached-X [C(1)DX] females and females from the heat shock to FM6 (y) males in accordance with an embodiment of the present invention. The percent of all the heat-shocked parents screened that gave at least one germline mutant is shown in parentheses in the # Giving y column. The total number of mutant flies recovered is given in the Total y column and also expressed as a percent of all candidate offspring (in parentheses). The number of mutant offspring per fly varied from 1 to 15. The ND data are from M. Bibikova et al. (2002) Genetics 161:1169-1175 which is hereby incorporated by reference.

DETAILED DESCRIPTION OF THE INVENTION

The present invention relates to methods and compositions for carrying out targeted genetic recombination or mutation. In contrast to previously known methods for targeted genetic recombination, the present invention is efficient and inexpensive to perform and is adaptable to any cell or organism. Any segment of double-stranded nucleic acid of a cell or organism can be modified by the method of the present invention. The method exploits both homologous and non-homologous recombination processes that are endogenous in all cells.

The method of the present invention provides for both targeted DNA insertions and targeted DNA deletions. The method involves transformation of a cell with a nucleic acid construct minimally comprising DNA encoding a chimeric zinc finger nuclease (ZFN). In a particular embodiment, the method further involves transforming a cell with a nucleic acid construct comprising donor DNA. Other schemes based on these general concepts are within the scope and spirit of the invention, and are readily apparent to those skilled in the art.

The present invention can be utilized in both somatic and germ cells to conduct genetic manipulation at a particular genetic locus.

In a particular embodiment, the present invention is utilized to disrupt a gene in a somatic cell wherein that gene is over-expressing a product and/or expressing a product that is deleterious to the cell or organism. Such gene may be over-expressed in one or more cell types resulting in disease. Disruption of such gene by the methods of the present invention may contribute to better health for an individual suffering from disease due to expression of such gene. In other words, disruption of genes in even a small percentage of cells can work to decrease expression levels in order to produce a therapeutic effect.

In another embodiment, the present invention can be utilized to disrupt a gene in a germ cell. Cells with such disruption in a particular gene can be selected for in order to create an organism without function of such gene. In such cell the gene can be completely knocked-out. The absence of function in this particular cell can have a therapeutic effect.

In another embodiment, the present invention can be utilized to enhance expression of a particular gene by the insertion of a control element into a somatic cell. Such control element may be a constitutively active, inducible or development stage-specific promoter. It may also be a tissue-specific promoter capable of effecting expression only in particular cell types. Such control element may be placed in such a manner to effect expression of a particular gene that is responsible for a product with a therapeutic effect in such a cell.

The present invention may further provide for the insertion of donor DNA encoding a gene product that, when constitutively expressed, has a therapeutic effect. An example of this embodiment would be to insert such DNA constructs into an individual suffering from diabetes in order to effect insertion of an active promoter and donor DNA encoding the insulin gene in a population of pancreatic cells. This population of pancreatic cells containing the exogenous DNA would then produce insulin, thereby aiding the diabetic patient. Additionally, such DNA constructs could be inserted into crops in order to effect the production of pharmaceutically-relevant gene products. Genes for protein products, such as insulin, lipase or hemoglobin, could be inserted into plants along with control elements, such as constitutively active or inducible promoters, in order to produce large amounts of these pharmaceuticals in a plant. Such protein products could then be isolated from the plant. Transgenic plants or animals may be produced with this method through a nuclear transfer technique (McCreath, K. J. et al. (2000) Nature 405:1066-1069; Polejaeva, I. A. et al., (2000) Nature 407: 86-90). Tissue or cell-type specific vectors may also be employed for providing gene expression only in the cells of choice.

Alternatively, the above-mentioned methods can be utilized in a germ cell in order to select cells where insertion has occurred in the planned manner in order for all subsequent cell divisions to produce cells with the desired genetic change.

As used herein, the cells in which genetic manipulation occurs and an exogenous DNA segment or gene has been introduced through the hand of man are called recombinant cells. Therefore, recombinant cells are distinguishable from naturally occurring cells which do not contain a recombinantly introduced exogenous DNA segment or gene. Recombinant cells include those having an introduced cDNA or genomic gene, and also include genes positioned adjacent to a heterologous promoter not naturally associated with the particular introduced gene.

To express a recombinant encoded protein or peptide, whether mutant or wild-type, in accordance with the present invention one would prepare an expression vector that comprises isolated nucleic acids under the control of, or operatively linked to, one or more promoters, which may be inducible, constitutively active or tissue specific, for example. To bring a coding sequence "under the control of" a promoter, one positions the 5' end of the transcription initiation site of the transcriptional reading frame generally between about 1 and about 50 nucleotides "downstream" (i.e., 3') of the chosen promoter. The "upstream" promoter stimulates transcription of the DNA and promotes expression of the encoded recombinant protein. This is the meaning of "recombinant expression" in this context.

Ways of effecting protein expression are well known in the art. One skilled in the art is capable of expression a protein of his or her choice in accordance with the present invention.

The methods of the present invention can be applied to whole organisms or in cultured cells or tissues or nuclei, including those cells, tissues or nuclei that can be used to regenerate an intact organism, or in gametes such as eggs or sperm in varying stages of their development. Because DSBs stimulate mutagenic repair in essentially all cells or organisms, cleavage by ZFNs may be used in any cells or organisms. The methods of the present invention can be applied to cells derived any organism, including but not limited to insects, fungi, rodents, cows, sheep, goats, chickens, and other agriculturally important animals, as well as other mammals, including, but not limited to dogs, cats and humans.

Additionally, the compositions and methods of the present invention may be used in plants. It is contemplated that the compositions and methods can be used in any variety of plant species, such as monocots or dicots. In certain embodiments, the invention can be used in plants such as grasses, legumes, starchy staples, *Brassica* family members, herbs and spices, oil crops, ornamentals, woods and fibers, fruits, medicinal plants, poisonous plants, corn, cotton, castor bean and any other crop specie. In alternative embodiments, the invention can be used in plants such as sugar cane, wheat, rice, maize, potato, sugar beet, cassava, barley, soybean, sweet potato, oil palm fruit, tomato, sorghum, orange, grape, banana, apple, cabbage, watermelon, coconut, onion, cottonseed, rapeseed and yam. In some embodiments, the invention can be used in members of the *Solanaceae* specie, such as tobacco, tomato, potato and pepper. In other embodiments, the invention can be used in poisonous ornamentals, such as oleander, any yew specie and rhododendron. In a particular embodiment, the *Brassica* specie is *Arabidopsis*.

Grasses include, but are not limited to, wheat, maize, rice, rye, triticale, oats, barley, sorghum, millets, sugar cane, lawn grasses and forage grasses. Forage grasses include, but are not limited to, Kentucky bluegrass, timothy grass, fescues, big bluestem, little bluestem and blue gamma. Legumes include, but are not limited to, beans like soybean, broad or Windsor bean, kidney bean, lima bean, pinto bean, navy bean, wax bean, green bean, butter bean and mung bean; peas like green pea, split pea, black-eyed pea, chick-pea, lentils and snow pea; peanuts; other legumes like carob, fenugreek, kudzu, indigo, licorice, mesquite, copaifera, rosewood, rosary pea, senna pods, tamarind, and tuba-root; and forage crops like alfalfa. Starchy staples include, but are not limited to, potatoes of any species including white potato, sweet potato, cassava, and yams. *Brassica*, include, but are not limited to, cabbage, broccoli, cauliflower, brussel sprouts, turnips, collards, kale and radishes. Oil crops include, but are not limited to, soybean, palm, rapeseed, sunflower, peanut, cottonseed, coconut, olive palm kernel. Woods and fibers include, but are not limited to, cotton, flax, and bamboo. Other crops include, but are not limited to, quinoa, amaranth, tarwi, tamarillo, oca, coffee, tea, and cacao.

Definitions

For the purposes of the present invention, the following terms shall have the following meanings:

As used herein, the term "targeted genetic recombination" refers to a process wherein recombination occurs within a DNA target locus present in a host cell or host organism. Recombination can involve either homologous or non-homologous DNA. One example of homologous targeted genetic recombination would be cleavage of a selected locus of host DNA by a zinc finger nuclease (ZFN), followed by homologous recombination of the cleaved DNA with homologous DNA of either exogenous or endogenous origin. One example of non-homologous targeted genetic recombination would be cleavage of a selected locus of host DNA by a ZFN, followed by non-homologous end joining (NHEJ) of the cleaved DNA.

As used herein, the terms "host cell" or "host organism" or, simply, "target host", refer to a cell or an organism that has been selected to be genetically transformed to carry one or more genes for expression of a function used in the methods of the present invention. A host can further be an organism or cell that has been transformed by the targeted genetic recombination or mutation methods of the present invention.

The term "target" or "target locus" or "target region" refers herein to the gene or DNA segment selected for modification by the targeted genetic recombination method of the present invention. Ordinarily, the target is an endogenous gene, coding segment, control region, intron, exon or portion thereof, of the host organism. However, the target can be any part or parts of the host DNA.

For the purposes of the present invention, the term "zinc finger nuclease" or "ZFN" refers to a chimeric protein molecule comprising at least one zinc finger DNA binding domain effectively linked to at least one nuclease capable of cleaving DNA. Ordinarily, cleavage by a ZFN at a target locus results in a double stranded break (DSB) at that locus.

For the purposes of the present invention, the term "marker" refers to a gene or sequence whose presence or absence conveys a detectable phenotype to the host cell or organism. Various types of markers include, but are not limited to, selection markers, screening markers and molecular markers. Selection markers are usually genes that can be expressed to convey a phenotype that makes an organism resistant or susceptible to a specific set of environmental conditions. Screening markers can also convey a phenotype that is a readily observable and distinguishable trait, such as Green Fluorescent Protein (GFP), GUS or beta-galactosidase. Molecular markers are, for example, sequence features that can be uniquely identified by oligonucleotide probing, for example RFLP (restriction fragment length polymorphism), or SSR markers (simple sequence repeat).

As used herein, the term "donor" or "donor construct" refers to the entire set of DNA segments to be introduced into the host cell or organism as a functional group. The term "donor DNA" as used herein refers to a DNA segment with sufficient homology to the region of the target locus to allow participation in homologous recombination at the site of the targeted DSB.

For the purposes of the present invention, the term "gene" refers to a nucleic acid sequence that includes the translated sequences that encode a protein ("exons"), the untranslated intervening sequences ("introns"), the 5' and 3' untranslated region and any associated regulatory elements.

For the purposes of the present invention, the term "sequence" means any series of nucleic acid bases or amino acid residues, and may or may not refer to a sequence that encodes or denotes a gene or a protein. Many of the genetic constructs used herein are described in terms of the relative positions of the various genetic elements to each other. For the purposes of the present invention, the term "adjacent" is used to indicate two elements that are next to one another without implying actual fusion of the two elements. Additionally, for the purposes of the present invention, "flanking" is used to indicate that the same, similar, or related sequences exist on either side of a given sequence. Segments described as "flanking" are not necessarily directly fused to the segment they flank, as there can be intervening, non-specified DNA between a given sequence and its flanking sequences. These and other terms used to describe relative position are used according to normal accepted usage in the field of genetics.

For the purposes of the present invention, the term "recombination," is used to indicate the process by which genetic material at a given locus is modified as a consequence of an interaction with other genetic material. For the purposes of the present invention, the term "homologous recombination" is used to indicate recombination occurring as a consequence of interaction between segments of genetic material that are homologous, or identical. In contrast, for purposes of the present invention, the term "non-homologous recombination" is used to indicate a recombination occurring as a consequence of interaction between segments of genetic material that are not homologous, or identical. Non-homologous end joining (NHEJ) is an example of non-homologous recombination.

Moreover, for the purposes of the present invention, the term "a" or "an" entity refers to one or more than one of that entity; for example, "a protein" or "an nucleic acid molecule" refers to one or more of those compounds, or at least one compound. As such, the terms "a" or "an", "one or more" and "at least one" can be used interchangeably herein. It is also to be noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated or biologically pure compound is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

Zinc Finger Nucleases

A zinc finger nuclease (ZFN) of the present invention is a chimeric protein molecule capable of directing targeted genetic recombination or targeted mutation in a host cell by causing a double stranded break (DSB) at the target locus. A ZFN of the present invention includes a DNA-binding domain and a DNA-cleavage domain, wherein the DNA binding domain is comprised of at least one zinc finger and is operatively linked to a DNA-cleavage domain. The zinc finger DNA-binding domain is at the N-terminus of the chimeric protein molecule and the DNA-cleavage domain is located at the C-terminus of said molecule.

A ZFN as herein described must have at least one zinc finger. In a preferred embodiment a ZFN of the present invention would have at least three zinc fingers in order to have sufficient specificity to be useful for targeted genetic recombination in a host cell or organism. A ZFN comprising more than three zinc fingers is within the scope of the invention. A ZFN having more than three zinc fingers, although more time-consuming to construct, would have progressively greater specificity with each additional zinc finger. In a particular embodiment, the DNA-binding domain is comprised of three zinc finger peptides operatively linked to a DNA cleavage domain.

The zinc finger domain of the present invention can be derived from any class or type of zinc finger. In a particular embodiment, the zinc finger domain comprises the $Cis_2His_2$ type of zinc finger that is very generally represented, for example, by the zinc finger transcription factors TFIIIA or Sp1. In a preferred embodiment, the zinc finger domain comprises three $Cis_2His_2$ type zinc fingers. The DNA recognition and/or the binding specificity of a ZFN can be altered in order to accomplish targeted genetic recombination at any chosen site in cellular DNA. Such modification can be accomplished using known molecular biology and/or chemical synthesis techniques. (see, for example, M. Bibikova et al. (2002) Genetics 161:1169-1175). ZFNs comprising zinc fingers having a wide variety of DNA recognition and/or binding specificities are within the scope of the present invention.

The ZFN DNA-cleavage domain is derived from a class of non-specific DNA cleavage domains, for example the DNA-cleavage domain of a Type II restriction enzyme. In a particular embodiment the DNA-cleavage domain is derived from the Type II restriction enzyme, FokI.

In a preferred embodiment, a ZFN comprises three $Cis_2His_2$ type of zinc fingers, and a DNA-cleavage domain derived from the type II restriction enzyme, FokI. According to this preferred embodiment, each zinc finger contacts 3 consecutive base pairs of DNA creating a 9 bp recognition sequence for the ZFN DNA binding domain. The DNA-cleavage domain of the preferred embodiment requires dimerization of two ZFN DNA-cleavage domains for effective cleavage of double-stranded DNA. (See, for example, J. Smith et al., (2000) Nucleic Acids Res. 28:3361-3369). This imposes a requirement for two inverted recognition (target DNA) sites within close proximity for effective targeted genetic recombination. If all positions in the target sites are contacted specifically, these requirements enforce recognition of a total of 18 base pairs of DNA. There may be a space between the two sites. The space between recognition sites for ZFNs of the present invention may be equivalent to 6 to 35 bp of DNA. The region of DNA between the two recognitions sites is herein referred to as the "spacer".

A linker, if present, between the cleavage and recognition domains of the ZFN comprises a sequence of amino acid residues selected so that the resulting linker is flexible. Or, for maximum target site specificity, linkerless constructs are made. A linkerless construct has a strong preference for binding to and then cleaving between recognition sites that are 6 bp apart. However, with linker lengths of between 0 and 18 amino acids in length, ZFN-mediated cleavage occurs between recognition sites that are between 5 and 35 bp apart.

For a given linker length, there will be a limit to the distance between recognition sites that is consistent with both binding and dimerization. (M. Bibikova et al. (2001) Mol. Cell. Biol. 21: 289-287). In a preferred embodiment, there is no linker between the cleavage and recognition domains, and the target locus comprises two nine nucleotide recognition sites in inverted orientation with respect to one another, separated by a six nucleotide spacer.

In order to target genetic recombination or mutation according to a preferred embodiment of the present invention, two 9 bp zinc finger DNA recognition sequences must be identified in the host DNA. These recognition sites will be in an inverted orientation with respect to one another and separated by about 6 bp of DNA. ZFNs are then generated by designing and producing zinc finger combinations that bind DNA specifically at the target locus, and then linking the zinc fingers to a cleavage domain of a Type II restriction enzyme.

Targeted Genetic Recombination or Mutation

The method of the present invention can be used for targeted genetic recombination or mutation of any cell or organism. Minimum requirements include a method to introduce genetic material into a cell or organism (either stable or transient transformation), sequence information regarding the endogenous target region, and a ZFN construct or constructs that recognizes and cleaves the target locus. According to some applications of the present invention, for example homologous recombination, donor DNA may also be required.

According to another application of the present invention, DNA encoding an identifiable marker will also be included with the DNA construct. Such markers may include a gene or sequence whose presence or absence conveys a detectable phenotype to the host cell or organism. Various types of markers include, but are not limited to, selection markers, screening markers and molecular markers. Selection markers are usually genes that can be expressed to convey a phenotype that makes an organism resistant or susceptible to a specific set of environmental conditions. Screening markers can also convey a phenotype that is a readily observable and distinguishable trait, such as Green Fluorescent Protein (GFP), beta-glucuronidase (GUS) or beta-galactosidase. Markers may also be negative or positive selectable markers. In a particular embodiment, such negative selectable marker is codA. Molecular markers are, for example, sequence features that can be uniquely identified by oligonucleotide probing, for example RFLP (restriction fragment length polymorphism), or SSR markers (simple sequence repeat).

The efficiency with which endogenous homologous recombination occurs in the cells of a given host varies from one class of cell or organism to another. However the use of an efficient selection method or a sensitive screening method can compensate for a low rate of recombination. Therefore, the basic tools for practicing the invention are available to those of ordinary skill in the art for a wide range and diversity of cells or organisms such that the successful application of such tools to any given host cell or organism is readily predictable. The compositions and methods of the present invention can be designed to introduce a targeted mutation or genetic recombination into any host cell or organism. The flexibility of the present invention allows for genetic manipulation in order to create genetic models of disease or to investigate gene function.

The compositions and methods of the present invention can also be used to effect targeted genetic recombination or mutation in a mammalian cell. In addition, a ZFN can be designed to cleave a particular gene or chromosomal locus, which is then injected into an isolated embryo prior to reimplantation into a female. ZFN-mediated DNA cleavage can occur either in the presence or absence of donor DNA. Offsprings can then be screened for the desired genetic alteration.

The compositions and methods of the present invention can also be used accomplish germline gene therapy in mammals. In one embodiment, ZFNs could be designed to target particular genes of interest. Eggs and sperm could be collected and in-vitro fertilization performed. At the zygote stage, the embryo could be treated with both a ZFN designed to target a particular sequence and a donor DNA segment carrying a sequence without the deleterious mutation. The embryo could then be returned to a female or a uterine alternative for the rest of the gestational period. In a particular embodiment, for example, the deleterious gene is the common cystic fibrosis (CF) allele delta F508. ZFNs and donor DNA are used according to the methods of the present invention in order to alleviate disease caused by a mutant gene. According to the method, eggs and sperm from known carrier parents are collected and in-vitro fertilized. After in-vitro fertilization, the zygote could be injected with ZFNs designed to target the delta F508 allele, and with donor DNA carrying the wild-type allele. The transformed zygote could then be reimplanted into the mother. With the compositions and methods of the present invention, such gene replacement would allow the offspring and all descendants to be free of the CF mutation.

In another embodiment, homologous recombination can be used as follows. First, a site for integration is selected within the host cell. Sequences homologous to the integration site are then included in a genetic construct, flanking the selected gene to be integrated into the genome. Flanking, in this context, simply means that target homologous sequences are located both upstream (5') and downstream (3') of the selected gene. These sequences should correspond to some sequences upstream and downstream of the target gene. The construct is then introduced into the cell, thus permitting recombination between the cellular sequences and the construct.

As a practical matter, the genetic construct will normally act as far more than a vehicle to insert the gene into the genome. For example, it is important to be able to select for recombinants and, therefore, it is common to include within the construct a selectable marker gene. The marker permits selection of cells that have integrated the construct into their genomic DNA. In addition, homologous recombination may be used to "knock-out" (delete) or interrupt a particular gene. Thus, another approach for inhibiting gene expression involves the use of homologous recombination, or "knock-out technology". This is accomplished by including a mutated or vastly deleted form of the heterologous gene between the flanking regions within the construct. Thus, it is possible, in a single recombinational event, to (i) "knock out" an endogenous gene, (ii) provide a selectable marker for identifying such an event and (iii) introduce a transgene for expression.

The frequency of homologous recombination in any given cell is influenced by a number of factors. Different cells or organisms vary with respect to the amount of homologous recombination that occurs in their cells and the relative proportion of homologous recombination that occurs is also species-variable. The length of the region of homology between donor and target affects the frequency of homologous recombination events, the longer the region of homology, the greater the frequency. The length of the region of homology needed to observe homologous recombination is also species specific. However, differences in the frequency of homologous recombination events can be offset by the sensitivity of selection for the recombinations that do occur. It will be appreciated that absolute limits for the length of the donor-target homology or for the degree of donor-target homology cannot be fixed but depend on the number of potential events that can be scored and the sensitivity of the selection for homologous recombination events. Where it is possible to screen $10^9$ events, for example, in cultured cells, a selection that can identify 1 recombination in $10^9$ cells will yield useful results. Where the organism is larger, or has a longer generation time, such that only 100 individuals can be scored in a single test, the recombination frequency must be higher and selection sensitivity is less critical. The method of the present invention dramatically increases the efficiency of homologous recombination in the presence of extrachromosomal donor DNA (see Examples). The invention can be most readily carried out in the case of cells or organisms that have rapid generation times or for which sensitive selection systems are available, or for organisms that are single-celled or for which pluripotent cell lines exist that can be grown in culture and which can be regenerated or incorporated into adult organisms. Rapid generation time is the advantage demonstrated for the fruit fly, *Drosophila*, in the present invention. The plant cells, *Arabidopsis* are one example of pluripotent cells that can be grown in culture then regenerated or incorporated into an intact organism. These cells or organisms are representative of their respective classes and the description demonstrates how the invention can be applied throughout those classes. It will be understood by those skilled in the art that the invention is operative independent of the method used to transform the organism. Further, the fact that the invention is applicable to such disparate organisms as plants and insects demonstrates the widespread applicability of the invention to living organisms generally.

Nucleic Acid Delivery

Transformation can be carried out by a variety of known techniques which depend on the particular requirements of each cell or organism. Such techniques have been worked out for a number of organisms and cells, and can be adapted without undue experimentation to all other cells. Stable transformation involves DNA entry into cells and into the cell nucleus. For single-celled organisms and organisms that can be regenerated from single-cells (which includes all plants and some mammals), transformation can be carried out in in vitro culture, followed by selection for transformants and regeneration of the transformants. Methods often used for transferring DNA or RNA into cells include forming DNA or RNA complexes with cationic lipids, liposomes or other carrier materials, micro-injection, particle gun bombardment, electroporation, and incorporating transforming DNA or RNA into virus vectors. Other techniques are well known in the art.

Examples of Some Delivery Systems Useful in Practicing the Present Invention

Liposomal Formulations:

In certain broad embodiments of the invention, the oligo- or polynucleotides and/or expression vectors containing ZFNs and, where appropriate, donor DNA, may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. Also contemplated are cationic lipid-nucleic acid complexes, such as lipofectamine-nucleic acid complexes. Lipids suitable for use according to the present invention can be obtained from commercial sources. Liposomes used according to the present invention can be made by different methods and such methods are known in the art. The size of the liposomes varies depending on the method of synthesis.

Microinjection: Direct microinjection of DNA into various cells, including egg or embryo cells, has also been employed effectively for transforming many species. In the mouse, the existence of pluripotent embryonic stem (ES) cells that are culturable in vitro has been exploited to generate transformed mice. The ES cells can be transformed in culture, then microinjected into mouse blastocysts, where they integrate into the developing embryo and ultimately generate germline chimeras. By interbreeding heterozygous siblings, homozygous animals carrying the desired gene can be obtained.

Adenoviruses: Human adenoviruses are double-stranded DNA tumor viruses with genome sizes of approximate 36 Kb. As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

Particular advantages of an adenovirus system for delivering DNA encoding foreign proteins to a cell include (i) the ability to substitute relatively large pieces of viral DNA with foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of recombinant virus; and (vi) the high infectivity of adenovirus.

In general, adenovirus gene transfer systems are based upon recombinant, engineered adenovirus which is rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both the E1 and E3 regions are capable of carrying up to 10 kB of foreign DNA and can be grown to high titers in 293 cells.

Other Viral Vectors as Expression Constructs. Other viral vectors may be employed as expression constructs in the present invention. Vectors derived from, for example, vaccinia virus, adeno-associated virus (AAV), and herpes viruses may be employed. Defective hepatitis B viruses, may be used for transformation of host cells. In vitro studies show that the virus can retain the ability for helper-dependent packaging and reverse transcription despite the deletion of up to 80% of its genome. Potentially large portions of the viral genome can be replaced with foreign genetic material. The hepatotropism and persistence (integration) are particularly attractive properties for liver-directed gene transfer. The chloramphenicol acetyltransferase (CAT) gene has been successfully introduced into duck hepatitis B virus genome in the place of the viral polymerase, surface, and pre-surface coding sequences. The defective virus was cotransfected with wild-type virus into an avian hepatoma cell line, and culture media containing high titers of the recombinant virus were used to infect primary duckling hepatocytes. Stable CAT gene expression was suvsequently detected.

Non-viral Methods. Several non-viral methods are contemplated by the present invention for the transfer into a host cell of DNA constructs encoding ZFNs and, when appropriate, donor DNA. These include calcium phosphate precipitation, lipofectamine-DNA complexes, and receptor-mediated transfection. Some of these techniques may be successfully adapted for in vivo or ex vivo use.

In one embodiment of the invention, the expression construct may simply consist of naked recombinant DNA. Transfer of the construct may be performed by any of the DNA transfer methods mentioned above which physically or chemically permeabilize the cell membrane. For example, polyomavirus DNA in the form of $CaPO_4$ precipitates was successfully injected into liver and spleen of adult and newborn mice which then demonstrated active viral replication and acute infection. In addition, direct intraperitoneal injection of $CaPO_4$ precipitated plasmid expression vectors results in expression of the transfected genes.

Transformation of Plants: Transformed plants are obtained by a process of transforming whole plants, or by transforming single cells or tissue samples in culture and regenerating whole plants from the transformed cells. When germ cells or seeds are transformed there is no need to regenerate whole plants, since the transformed plants can be grown directly from seed. A transgenic plant can be produced by any means known in the art, including but not limited to *Agrobacterium tumefaciens*-mediated DNA transfer, preferably with a disarmed T-DNA vector, electroporation, direct DNA transfer, and particle bombardment. Techniques are well-known to the art for the introduction of DNA into monocots as well as dicots, as are the techniques for culturing such plant tissues and regenerating those tissues. Regeneration of whole transformed plants from transformed cells or tissue has been accomplished in most plant genera, both monocots and dicots, including all agronomically important crops.

Screening for Mutations

Methods for genetic screening to accurately detect mutations in genomic DNA, cDNA or RNA samples may be employed, depending on the specific situation. A number of different methods have been used to detect point mutations, including denaturing gradient gel electrophoresis ("DGGE"), restriction enzyme polymorphism analysis, chemical and enzymatic cleavage methods, and others. The more common procedures currently in use include direct sequencing of target regions amplified by PCR™ and single-strand conformation polymorphism analysis ("SSCP"). SSCP relies upon the differing mobilities of single-stranded nucleic acid molecules of different sequence on gel electrophoresis. Techniques for SSCP analysis are well known in the art.

Another method of screening for point mutations is based on RNase cleavage of base pair mismatches in RNA/DNA and RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single and multiple base point mutations.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Induction of Targeted Mutations

Zinc Finger Design

A pair of ZFNs were designed and constructed for a chomomosomal target locus in the yellow (y) gene of *Drosophila*. Zinc fingers generally bind preferentially to G-rich regions of DNA, and extensive study has been performed of fingers that bind all 5'-GNN-3' triplets (Segal et al. (1999) PNAS USA 96:2758-2763). Because the binding sites must be in an inverted orientation with respect to each other for effective cleavage by ZFNs (Bibikova et al. (2001) Mol. Cell. Biol. 21:289-297), the chromosomal target locus of *Drosophila* (y) was searched for inverted recognition sequences of the form $(NNC)_3 \ldots (GNN)_3$. Such a site was identified in exon 2 with a 6-bp separation between the component 9-mer recognition sites, which is the optimal spacer for specific recognition and cleavage by ZFNs that have no added linker or spacer between the binding and cleavage domains (M. Bibikova et al. (2001) Mol. Cell. Biol. 21: 289-287). The specific recognition sequences of the two ZFNs are described in Bibikova et al. 2002, Genetics 161: 1169-1175. DNAs encoding zinc fingers that recognize the DNA sequences, 5'-GCGGATGCG-3' (SEQ ID NO:1) and 5'-GCGGTAGCG-3' (SEQ ID NO:2), were obtained from Drs. David Segal and Carlos Barbas (Scripps Research Institute, La Jolla, Calif.) (Segal, D. J., et al. (1999) PNAS 96, 2758-2763). The DNAs encoding the zinc fingers were then modified using mutagenic PCR primers, and two sets of three zinc fingers each were produced: one, referred to as yA that recognizes one of the component 9-mers of the y gene target (5'-GTG-GATGAG-3' (SEQ ID NO: 3)), and another, referred to as yB, that recognizes the other component 9-mer of the y gene target (5'-GCGGTAGGC-3' (SEQ ID NO: 4)). Two fingers were modified in yA, but only one in yB. DNA encoding each of the resulting 3-finger sets of zinc fingers were both cloned in frame with the FokI DNA cleavage domain in the pET15b expression plasmid, with no intervening linker DNA between the DNA recognition and cleavage domains. Both chimeric ZFN proteins were expressed, purified by Ni-affinity chromatography, and tested for cleavage activity in vitro by methods described previously (Smith, J., et al. (2000) Nucleic Acids Res. 28, 3361-3369; and Bibikova, M., et al. (2001) Mol. Cell. Biol. 21, 289-297), using the pS/G plasmid (Geyer, P. K & Corces, V. G. (1987) Genes Dev. I, 996-1004), which carries the complete y gene. Together the two ZFNs made a single double stranded break (DSB) at the expected site in a 10.7-kb plasmid DNA carrying the y gene.

P Element Vectors and Transformation of Fly Larvae.

The yA and yB ZFN coding sequences were then cloned separately behind the *Drosophila* Hsp70 heat shock promoter by insertion of ZFN DNA between the BamHI and SalI sites of a modified phsp70 plasmid (Petersen, R. B. & Lindquist, S. (1989) Cell. Regul. 1, 135-149). A fragment carrying the heat shock promoter and ZFN DNA sequences was excised by partial HindIII and complete ApaI digestion and cloned between these same endonuclease sites in the commercially available cloning vector, pBluescript. After verification of the sequence of the insert, it was excised by digestion with NotI and inserted into the ry+ P element vector pDM30 (Mismer, D. & Rubin, G. M. (1987) Genetics 116, 565-578). The resulting yA and yB plasmids were injected separately into v ry embryos, along with the P-transposase expression plasmid pπ25.lwc, and eclosing adults were mated to screen for ry+ germline transformants. The ry+ insertion was mapped to a specific chromosome for multiple independent transformants with each ZFN. Both balanced and homozygous stocks were created for several lines carrying yA and yB without viability problems in most cases. Genes for the two ZFNs were brought together (as described in the Examples below) with appropriate crosses of mature flies, and the offspring were heat shocked 4 days after the initiation of mating by immersing the glass vials containing the flies in a water bath at 35° for one hour. As adults eclosed they were screened for evidence of somatic y mutations. Control vials from crosses involving each nuclease separately were subjected to the heat shock, and yA+yB flies that had not been heat shocked were also screened.

Recovery of Germline Mutants.

All flies emerging from the heat shock protocol and carrying both the yA and yB nucleases were mated to reveal potential germline mutations. Males were crossed with 2 or 3 attached-X [C(1)DX] females, and the resulting male offspring screened for yellow body color. Females were crossed with 2 or 3 y (FM6) males, and the resulting offspring of both genders screened. Mutants were identified and all of them were males that had originated from male parents. These identified mutant male offspring were then crossed to C(1)DX females to produce additional progeny carrying the same mutation.

DNA Analysis.

The presence or absence of the target DNA was identified by DNA analysis. Individual flies were homogenized in 100 μl of a 1:1 mixture of phenol and grind, buffer (7 M urea, 2% SDS, 10 mM Tris, pH 8.0, 1 mM EDTA, 0.35 M NaCl) preheated to 60°. Each sample was extracted with 50 μl of chloroform, the organic phase back-extracted with 100 μl of grind buffer, and the combined aqueous phases re-extracted with 50 μl of chloroform. DNA was precipitated with ethanol and re-dissolved in 20 μl of 10 mM Tris, pH 8.5. A 600-bp DNA fragment was amplified by PCR with primers flanking the yA+yB recognition site. The primers were called YF2 (5'ATTCCTTGTGTCCAAAATAATGAC-3' (SEQ ID NO:5)) and YR3 (5'-AAAATAGGCATATGCATCATCGC3' (SEQ ID NO:6)) For the larger deletions, YR3 was used in combination with a more distant sequence, YF1 (5'ATTTTG-TACATATGTTCTTAAGCAG-3' (SEQ ID NO:7)). Amplified fragments were recovered after gel electrophoresis, and DNA sequences were determined at the University of Utah DNA Sequencing Core Facility with an ABI3700 capillary sequencer and the YR3 primer.

Induction of Targeted y Mutations Resulting from Double Stranded Breaks and Nonhomologous End Joining The levels of expression of yA induced at 37° were found, in several independent transformants, to be lethal when applied at larval and embryonic stages. Moderating the heat shock to 35° allowed survival of a good proportion of the yA-carrying flies. The yB ZFN did not affect viability at any temperature tested.

After individual flies carrying the yA and yB nucleases on the same chromosome were crossed and their progeny heat-shocked, offspring demonstrating y mosaic, as well as germline mutations were observed in male offspring. In males (except following DNA replication), only simple religation or NHEJ would be available to repair the damage after a DSB. In *Drosophila*, as in many other eukaryotes, NHEJ frequently produces deletions and/or insertions at the joining site. Since the DSB is targeted to protein coding sequences in y+, most such alterations would lead to frameshifts or to deletion of essential codons, which can lead to a phenotype of patches of y mutant tissue.

Somatic yellow mosaics were identified in multiple yA+yB males. Most of the patches were in the distal abdominal cuticle and bristles, but some examples in leg, wing and scutellar bristles were also observed. No other phenotypic defects have been seen on a regular basis. The frequency of somatic mosaics was quite high. In pooled data from crosses involving a number of independent yA and yB lines, 105 of 228 candidate males (46%) showed obvious y patches. For some yA+yB combinations the frequency was greater than 80%. No yellow mosaics were observed in controls with a single nuclease or without heat shock. This indicates that the yA+yB ZFNs are capable of inducing somatic mutations at their designated target.

Characterization of Germline y Mutations.

To isolate germline y mutations, all yA+yB males from several heat shock experiments were crossed to females carrying an attached-X chromosome [C(1)DX/Y], in order to produce male offspring that were known to only receive their father's X chromosome. In total, 228 male fathers yielded 5,870 sons; 26 of the male off-spring, from 13 different fathers, were clearly y throughout their entire bodies. Thus, 5.7% of the yA+yB male fathers produced at least one germline mutant. Of the 13 fathers, 6 had been identified as having y somatic patches, while the other 7 appeared to be entirely y+ in diagnostic features. No y flies were isolated among 7050 progeny of 125 heat-shocked yA+yB females crossed to y males. The ZFNs appear to be effective in inducing mutations via NHEJ most efficiently in the male germline.

DNA was isolated from the 13 fathers identified above and 5 additional males in order to analyze each of them for the presence of the target DNA. A 600-bp fragment including the expected cleavage site was amplified by PCR. In three of the 18 male flies, the binding site for one of the primers had been deleted, and a new primer had to be generated in order to accomplish amplification. This new primer was located at a more distant location. Sequence analysis of all fragments revealed unique alterations precisely at the target site. Nine of the sequenced mutants had simple deletions; five had deletions accompanied by insertions; and three were simple, short duplications. Three of the deletions extended for hundreds of bps to one side of the target and these were the three samples that required a new primer design. These are exactly the types of mutations that were expected to result from NHEJ after cleavage by the yA+yB ZFNs, and they are very similar to those produced after P element excision. Some of the frameshift y mutations created a stop codon within a short distance of the alteration, while one inserted an asparagine codon into the normal reading frame.

Targeted Cleavage and Mutagenesis.

This example demonstrated that ZFNs can be designed to produce DSBs in target chromosomal locus in an exemplary genome in order to produce a permanent genetic alteration. The frequency of observed somatic mutation was quite high, and the real number of somatic mosaics may be even higher, since y mutations have no effect on many visible features. This was corroborated by the recovery of germline mutations from phenotypically y+ parents.

In this particular Example, germline mutations were recovered only in males and at a lower frequency than somatic mosaics.

Example 2

ZFN-Induced Double Stranded Breaks Stimulate Targeted Genetic Recombination in the Presence of Homologous Donor DNA Zinc Finger and Donor DNA Design A pair of ZFNs were designed and constructed for a chomomosomal target locus in the yellow (y) gene of *Drosophila* as described in Example 1.

In order to make an identifiable donor DNA for the *Drosophila* gene, y, the yA and yB recognition sites for the zinc fingers were replaced with two in-frame stop codons and an XhoI site. These changes were introduced by amplification with PCR primers carrying the desired sequence. Relative to the wild type y, 21 bp were deleted leaving only 3 bp of the yA recognition site, and a 9 bp replacement inserted the two in-frame stop codons and inserted the XhoI site. This mutant (yM) carries a total of 8 kb of homology to the y locus. It was inserted into a P element vector and introduced into the fly genome. The yM sequence is flanked by recognition sites for the FLP recombinase (FRT) and the meganuclease I-SceI to permit excision and linearization of the donor. Generating a linear extrachromosomal donor DNA in situ by this means has been shown to enhance its effectiveness in recombination (Y. S. Rong and K. G. Golic, Science 288, 2013-2018 (2000)).

Experimental Design

The design of the targeted genetic recombination experiment is as follows: The $y^+$ target lies on the X chromosome. The transgenes for the yA and yB ZFNs are on one chromosome 2, while those for FLP and/or I-SceI (when present) are on the other chromosome 2. The donor DNA (yM) is located on chromosome 3 in a p-element vector that also carries the white gene ($W^+$). Each of these inserted genes is under the control of a *Drosophila* HSP70 promoter. Upon heat-shock induction, the ZFNs will cut their target at y. This broken chromosome can be restored to wild type, or it can acquire a y mutation either by NHEJ or by homologous recombination. When neither FLP nor I-SceI is present, the donor remains integrated. When FLP is expressed, the donor is excised as an extrachromosomal circle. When I-SceI is also expressed, it converts the donor to an ends-out linear molecule which can recombine with the cleaved target locus. Experiments were also performed with linear donor only in the absence of yA and yB (and therefor without cleavage of the target).

Larvae carrying single copies of these introduced DNA components were heat-shocked at 35°, for one hour, 0-4 days after egg laying. The experiment contained five groups as exemplified below:

ND, no donor: yA+yB only;
ID, integrated donor: yA+yB+donor, no FLP or I-SceI;
CD, circular extrachromosomal donor: yA+yB+FLP+donor,
LD, linear extrachromosomal donor: yA+yB+FLP+I-SceI+donor,
DO, linear donor only: FLP+I-SceI+donor, but no ZFNs.

Adults emerging from the heat shock protocol were crossed to reveal germline y mutations. The frequencies of germline y mutations resulting from the heat-shock treatment are shown in Table 1 in column 3. The frequencies of mutation rose in both males and females in the presence of the donor and the frequency increased further with extrachromosomal and linear DNA. With linear extrachromosomal DNA, nearly 20% of males and 14% of females yielded at least one mutant offspring.

The y mutations were propagated in further crosses, chromosomal DNA was recovered. The frequency of germline y mutants and the proportion due to either NHEJ or homologous recombination with the donor DNA was determined by PCR amplification of 600 bp of DNA including the target region of the y gene followed by XhoI digestion of the amplified product. Products of homologous recombination between donor and target were recognized by XhoI digestion of the PCR fragment; some of these and many of the XhoI-resistant products were sequenced. The latter showed small deletions and/or insertions and occasionally larger deletions, all of which are characteristic of NHEJ.

The fourth column of Table 1 reports the recovery of germline mutants as a percentage of all offspring. The fractions of those mutations resulting from either NHEJ or homologous recombination with the donor rose as the donor DNA became more effective at participating in homologous recombination: linear donor DNA being more effective than circular donor DNA, which was more effective than integrated donor DNA. The integrated donor, located on chromosome 3, was not very effective in serving as a template for repair of the break at y and the majority of recovered mutations were due to NHEJ. The circular donor was much more effective and approximately ⅓ of all mutations were determined to be due to gene replacements. With the linear donor, more than 2% of all sons of males were mutant, and 63% of these were products of homologous recombination. In the female germline 73% of y mutations were homologous replacements. Target cleavage by chimeric ZFNs stimulates targeted genetic recombination substantially, and the most effective way to integrate donor DNA into a host organism's genome is with linear donor DNA.

The ZFN-induced targeted genetic recombination results differ from those obtained without targeted cleavage in several respects. First, induced mutations were found in both the male and female germlines, while only females had yielded good frequencies in previous trials by other researchersError! Bookmark not defined. Apparently the presence of a DSB in the target activates recombination processes in males that are not efficient on intact chromosomes. The lower targeting frequencies observed in females may reflect the possibility of repairing the break by recombination with an uncut homologous X chromosome. Second, the overall frequency of induced mutations was about 10-fold higher in males in the linear DNA and circular DNA experiments than was seen earlier at y in females with an ends-in donor: approximately 1/50 gametes, compared to 1/500 gametes. Even in the female germline, the frequency of ZFN-induced mutations was 1/200 gametes, and 3/4 of these were gene replacements. Thus, the presence of a homologue donor does not preclude interaction with the extrachromosomal donor. Third, deletions and insertions due to NHEJ were also observed, in addition to the targeted homologous recombinants. Such products were not expected nor observed in the absence of target cleavage.

Example 3

Expression of Chimeric ZFNs in *Arabidopsis* in Order to Stimulate Induction of Targeted Mutations Experimental Design: The method of the present invention will be used to target and knock out the *Arabidopsis* TRANSPARENT TESTA GLABRA1 gene (TTG1, gene number AT5G24520 (GenBank number AJ133743). An EST for this gene has been sequenced (GenBank numbers F20055, F20056). The gene encodes a protein containing WD40 repeats (Walker et al. (1999) Plant Cell 11, 1337-1349).

Two chimeric DNA constructs will be generated consisting of (1) nucleic acid sequence encoding the promoter region from the *Arabidopsis* HSP18.2 gene and (2) nucleic acid sequence encoding zinc finger proteins specific for the TTG1 gene operatively linked to a nucleic acid sequence encoding a non-specific endonuclease. The HSP18.2 promoter will confer expression in *Arabidopsis* and gene expression will be controlled by heat-shocking the resulting plants. The chimeric genes will be referred to as HS::ZnTTG1 A and HS::ZnTTG1B. These two genes can be incorporated into the same *Agrobacterium* vector.

All of our experiments will be carried out using the model genetic organism *Arabidopsis thaliana*, because of a number of desirable features of this system including small size, small genome, and fast growth. A ttg1 mutant has a distinctive phenotype, making it an excellent exemplary model. For instance, ttg1 mutants are glabrous and mutant plants lack trichomes on leaves and stems. Trichomes are hair-like outgrowths from the epidermis.

Additionally, ttg1 mutant are defective in flavonoid production. Flavonoids are a complex class of compounds including purple anthocyanin pigments and tannins. TTG1 protein positively regulates synthesis of the enzyme dihydroflavonol reductase, which is required for production of both anthocyanins and tannins (Shirley et al. (1995) Plant Journal 8:659-671; Pelletier and Shirley (1996) Plant Physiology 111:339-345).

These ttg1 mutants also have a transparent testa or seed coat. In wild type, the seed coat (inner layer of the inner integument) has dense, brown tannin and ttg1 mutants lack this pigment. As a consequence, the seed coat of seed collected from ttg1 mutants are transparent, and seed collected from ttg1 mutants are yellow because the yellow embryos show through the transparent seed coat.

These ttg1 mutants also lack anthocyanins. In wild type, seedlings, stems, and leaves produce reddish/purple anthocyanin pigments, particularly under stress. These pigments are absent in ttg1 mutants.

Additionally, ttg1 mutants produce extra root hairs. In wild type, root hairs are produced only from trichoblast cells. In ttg1 mutants, by contrast, root hairs are produced by both tricoblast cells and atrichoblast cells. The result is a root that appears more hairy (Galway et al. (1994) Developmental Biology 166, 740-754).

The ttg1 mutants also fail to produce mucilage in the outer layer of the seed coat. Mucilage is a complex carbohydrate, sometimes called slime that covers the seed coat. Lastly, the ttg1 mutants have altered dormancy and ttg1 seeds do not require drying out or cold treatments to germinate.

The presence of all seven characteristics makes visual screening for this mutant genotype an easy task.

Design of Zinc Fingers

The TTG1 gene was scanned for sequences of the form: NNY NNY NNY NNNNNN RNN RNN RNN, where Y is either T or C, R is A or G, and N is any base. This identified sequences comprised of triplets that are initiated by an A or G in opposite orientation—i.e., on opposite strands—and separated by exactly 6 bp. This has been shown to be a preferred structure for zinc finger nuclease recognition and cleavage (M. Bibikova et al. (2001) Mol. Cell. Biol. 21: 289-287).

The component triplets of the sequences identified in 1 were then classified according to whether there were zinc fingers that were known to bind them specifically. Two sites in TTG1 were identified as potential ZFN binding and cleavage sites: 5'-TCC GGT CAC AGA ATC GCC GTC GGA-3' (SEQ ID NO:8), and 5'-ACT TCC TTC GAT TGG AAC GAT GTA3' (SEQ ID NO:9) (at nucleotide 406 in the TTG1 sequence).

Zinc finger nucleases comprising a binding domain designed to bind the first of these sites will be constructed either by oligonucleotide synthesis and extension (Segal, D. J. (2002) Methods 26:76-83.), or by PCR with mutagenic primers (M. Bibikova et al., (2002) Genetics 161:1169-1175). The resulting coding sequences will be inserted into plasmids vectors in frame with the FokI nuclease domain to create two ZFN coding sequences, ZnTTG1A and ZnTTG1B. The encoded proteins will be expressed in *E. coli* and partially purified (M. Bibikova et al. (2002) Genetics 161:1169-1175). The recovered ZFNs will be tested in vitro for the ability to cleave plasmid DNA encoding the TTG1 gene. Success in this assay will be evidenced by no cleavage by either ZFN alone, but cleavage at the expected site by a mixture of the two ZFNs.

Transformation:

The HS::ZnTTG1A and HS::ZnTTG1 B genes will be introduced into the *Arabidopsis* genome using *Agrobacterium*-mediated transformation. To do so, the HS::ZnTTG1A and B genes will be inserted into an *Agrobacterium* T-DNA transformation vector (pCAMBIA1380) that harbors a selectable hygromycin resistant marker. A pCAMBIA HS::ZnTTG1 clone will then be introduced into *Agrobacterium* cells using standard *Agrobacterium* transformation procedures, and the HS::ZnTTG1A and HS::ZnTTG1B genes will then be introduced into *Arabidopsis* plants using the standard floral dip method. (See, Clough, S, and Bent, A (1999) Plant Journal 16:735-743).

Induction of Expression of ZFNs in a Host Cell

Seeds from the T1 generation will be collected from the dipped plants. In order to select for transformed seedlings, the T1 seeds will be germinated on agar plates containing the antibiotic hygromycin. Approximately four days after germination, the plates containing the germinated seedlings will be wrapped in plastic wrap and immersed in 40° C. water for two hours to induce expression of the ZFN genes. At approximately two weeks following germination, the hygromycin resistant transformed seedlings will be transferred to dirt.

Screening for Gene-Targeting Event:

Screening Method 1: The HS::ZnTTG1 genes will be introduced into wild-type *Arabidopsis* plants and the T1 plants will be heated as described above. At 1-2 weeks following heat treatment, a sample of tissue will be harvested from heat-treated plants and DNA extracted from this tissue. PCR amplification using 20 bp primers flanking the zinc finger target site (25 bp on each side of the target site) will be utilized to determine if the HS::ZnTTG1 gene is present. The PCR band from control plants that were not heat treated should be approximately 90 bp in size. PCR bands from the heat-treated plants should include smaller products than 90 bp that result from the existence of deletions surrounding the zinc finger target site. To verify the existence of small deletions, we will clone and determine the DNA sequence of the smaller PCR products.

Screening Method 2: The HS::ZnTTG1 A and HS::ZnTTG1 B genes will be introduced into wild-type *Arabidopsis* plants and the T1 plants will be heat-treated as described above. The T1 plants will be grown to maturity, allowed to self pollinate, and T2 seeds will be collected. The T2 seeds will be grown on agar plates and they will be scored for seedling phenotypes including hairless leaves (glabrous phenotype), brighter leaves (anthrocyanin minus phenotype), and hairy roots, as described above. Mutant plants will be transferred to dirt and grown further. Tissue from mutant plants will be harvested and DNA extracted in preparation for PCR-screening as described above. Briefly, PCR will be performed with primers flanking the zinc finger target sites and samples exhibiting approximately 90 bp products were not transformed, whereas those exhibiting products less than 90 bp were transformed. This is due to the existence of deletions surrounding the zinc finger target site. Additionally, small insertions or much larger deletions may be present around the zinc finger target site, as well. To verify the existence of these occurrences, we will clone and determine the DNA sequence of the smaller PCR to products.

Screening Method 3: The HS::ZnTTG1 A and HS::ZnTTG1 B genes will be introduced into heterozygous ttg1 mutants (i.e., genotype ttg1/TTG1). The male sterile1 (ms1) plants will be introduced to the *Agrobacterium* solution (note: the ms1 and ttg1 loci are linked, 6 cM apart on chromosome 5). The dipped plants then will be pollinated with pollen from homozygous ttg1-1 plants. The crossed plants will be allowed to mature, the resultant T1/F1 seeds collected, and the T1/F1 seeds allowed to germinate in the presence of hygromycin. Surviving T1/F1 seedlings will contain the HS::ZnTTG1 transgene and will be heterozygous at the ttg1 locus genotype MS1-ttg1-1/ms1-TTG1). The T1/F1 plants will be heat-shocked as described above. In a subset of cells, the wild-type allele will be knocked out, resulting in a sector of homozygous ttg1 (i.e., genotype ttg1-1/ttg1-ko) cells. These mutant sectors will be detectable (and, thus, a targeted genetic recombination event) by visualizing several phenotypes, such as hairless leaves (glabrous phenotype), brighter leaves (anthocyanin minus phenotype), and yellow seeds (transparent testa phenotype). Tissue will be collected from mutant sectors and targeting verified using the PCR-cloning-sequencing strategy discussed above. From the mutant sectors, T2 seeds will be collected and grown into T2 plants. In the T2 generation, the phenotype will be verified: plants homozygous for the knockout allele (i.e., ttg1-ko) also will be homozygous for the ms1 mutation and, thus, will be male sterile (i.e., genotype ms1-ttg1-ko/ms1-ttg1-ko). Tissue from the double mutants (phenotypically ttg1 and ms1) will be harvested and verified for targeting using the PCR-cloning-sequencing strategy discussed above.

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

TABLE 1

Recovery of germline y mutations

| 1<br>Donor | 2<br># Screened | 3<br># Giving y | 4<br>Total y |
|---|---|---|---|
| Females: | | | |
| ND | 125 | 0 (0%) | 0 |
| ID | 188 | 9 (4.8%) | 15 (0.16%) |
| CD | 309 | 31 (10%) | 59 (0.38%) |
| LD | 503 | 68 (13.5%) | 135 (0.54%) |
| DO | 158 | 1 (0.6%) | 2 (0.02%) |
| Males: | | | |
| ND | 228 | 13 (5.7%) | 24 (0.42%) |
| ID | 218 | 24 (11%) | 40 (0.73%) |
| CD | 261 | 49 (19%) | 104 (1.59%) |
| LD | 522 | 94 (18%) | 292 (2.24%) |
| DO | 177 | 1 (0.6%) | 1 (0.02%) |

We claim:

1. A method of targeted genetic recombination in host plant cell comprising: introducing into a host plant cell a nucleic acid molecule encoding a Zinc Finger Nuclease (ZFN) targeted to a chosen host chromosomal target locus; inducing expression of the ZFN within the host cell; and identifying a host cell in which the chosen host chromosomal target locus exhibits a mutation.

2. The method of claim 1 wherein the mutation is a deletion of genetic material.

3. The method of claim 1 wherein the mutation is an insertion of genetic material.

4. The method of claim 1 wherein the mutation is both a deletion and an insertion of genetic material.

5. The method of claim 1 further comprising introducing donor DNA into the host cell.

6. The method of claim 5 wherein the donor DNA provides a gene sequence that encodes a product to be produced in the host cell.

7. The method of claim 6 wherein the donor DNA provides a gene sequence that encodes a product selected from the group consisting of pharmaceuticals, hormones, proteins, nutriceuticals or chemicals.

8. The method of claim 1 wherein the plant is a monocotyledon.

9. The method of claim 8 wherein the plant is selected from the group consisting of maize, rice or wheat.

10. The method of claim 1 wherein the plant is a dicotyledon.

11. The method of claim 10 wherein the plant is selected from the group consisting of tobacco, potato, soybean, tomato, members of the *Brassica* family, or *Arabidopsis*.

12. The method of claim 1 wherein the plant cell is from a tree.

13. A method of targeted genetic recombination in a plant host cell comprising selecting a zinc finger DNA binding domain capable of preferentially binding to a specific host target locus to be mutated; selecting a nucleic acid encoding a non-specific DNA cleavage domain capable of cleaving double-stranded DNA when operatively linked to said binding domain and introduced into the plant host cell; selecting an inducible control element capable of inducing expression in the host cell; operatively linking the selected nucleic acid encoding the zinc finger the DNA binding domain and the selected nucleic acid encoding the cleavage domain and the inducible control element to produce a DNA construct; introducing said DNA construct into a target host cell; and identifying at least one host cell exhibiting recombination at the target locus in the host DNA.

14. The method of claim 13 further comprising introducing donor DNA into the host cell.

15. The method of claim 14 wherein the donor DNA provides a gene sequence that encodes a product to be produced in the host cell.

16. The method of claim 15 wherein the donor DNA provides a gene sequence that encodes a product selected from the group consisting of pharmaceuticals, hormones, proteins, nutriceuticals or chemicals.

17. The method of claim 13 wherein the DNA binding domain is comprised of three zinc fingers.

18. The method of claim 13 wherein the zinc fingers DNA binding domain is a Cis2His2 zinc finger.

19. The method of claim 13 wherein the cleavage domain is from a Type II restriction endonuclease.

20. The method of claim 19 wherein the Type II restriction endonuclease is FokI.

21. The method of claim 13 wherein the inducible control element is a heat-shock inducible control element.

22. The method of claim 14 wherein the plant is a monocotyledon.

23. The method of claim 22 wherein the plant is selected from the group consisting of maize, rice or wheat.

24. The method of claim 14 wherein the plant is a dicotyledon.

25. The method of claim 24 wherein the plant is selected from the group consisting of tobacco, potato, Soybean, tomato, members of the *Brassica* family, or *Arabidopsis*.

26. The method of claim 14 wherein the plant is a tree.

27. The method of claim 14 wherein the DNA construct further comprises DNA encoding one or more selectable marker.

28. The method of claim 27 wherein the selectable marker provides positive selection for cells expressing the marker.

29. The method of claim 27 wherein the selectable marker provides negative selection for cells expressing the marker.

30. The method of claim 27 wherein the selectable marker provides positive and negative selection for cells expressing the marker.

31. The method of claim 13 wherein the plant is a monocotyledon.

32. The method of claim 31 wherein the plant is selected from the group consisting of maize, rice or wheat.

33. The method of claim 13 wherein the plant is a dicotyledon.

34. The method of claim 33 wherein the plant is selected from the group consisting of tobacco, potato, soybean, tomato, members of the *Brassica* family, or *Arabidopsis*.

35. The method of claim 13 wherein the plant is a tree.

36. The method of claim 13 wherein the one host cell exhibiting recombination is a somatic cell of the organism.

37. The method of claim 14 wherein the DNA binding domain is comprised of three zinc fingers.

38. The method of claim 14 wherein the cleavage domain is a Type II restriction endonuclease.

39. The method of claim 14 wherein the inducible control element is a heat-shock inducible control element.

* * * * *